(12) United States Patent
Block et al.

(10) Patent No.: US 12,097,372 B2
(45) Date of Patent: *Sep. 24, 2024

(54) TARGETED ELECTROSTIMULATION FIELDS BASED ON FOCAL DERMATOMAL COVERAGE

(71) Applicant: Boston Scientific Neuromodulation Corporation, Valencia, CA (US)

(72) Inventors: Jessica Block, Sherman Oaks, CA (US); Tianhe Zhang, Studio City, CA (US); Natalie A. Brill, Sherman Oaks, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 290 days.

This patent is subject to a terminal disclaimer.

(21) Appl. No.: 17/706,867

(22) Filed: Mar. 29, 2022

(65) Prior Publication Data

US 2022/0218995 A1 Jul. 14, 2022

Related U.S. Application Data

(63) Continuation of application No. 16/879,018, filed on May 20, 2020, now Pat. No. 11,331,491.

(Continued)

(51) Int. Cl.
*A61N 1/36* (2006.01)

(52) U.S. Cl.
CPC ..... *A61N 1/36071* (2013.01); *A61N 1/36171* (2013.01); *A61N 1/36175* (2013.01); *A61N 1/36192* (2013.01)

(58) Field of Classification Search
CPC ............ A61N 1/36062; A61N 1/36071; A61N 1/36132; A61N 1/36171; A61N 1/36175; A61N 1/36185; A61N 1/36192
See application file for complete search history.

(56) References Cited

U.S. PATENT DOCUMENTS 8,620,452 B2  12/2013  King et al.
9,814,880 B2  11/2017  Hershey et al.
(Continued)

OTHER PUBLICATIONS

"U.S. Appl. No. 16/879,018, 312 Amendment filed Feb. 2, 2022", 8 pgs.

(Continued)

*Primary Examiner* — George Manuel
(74) *Attorney, Agent, or Firm* — Schwegman Lundberg & Woessner, P.A.

(57) ABSTRACT

Systems and methods for optimizing neuromodulation field design for pain therapy are discussed. An exemplary neuromodulation system includes an electrostimulator to stimulate target tissue to induce paresthesia, a data receiver to receive pain data including pain sites experiencing pain, and to receive patient feedback on the induced paresthesia including paresthesia sites experiencing paresthesia. The neuromodulation system includes a processor circuit configured to generate a spatial correspondence indication between the pain sites and the paresthesia sites over one or more dermatomes, determine an anodic weight and a cathodic weight for each of multiple electrode locations using the spatial correspondence indication, and generate a stimulation field definition for neuromodulation pain therapy.

20 Claims, 22 Drawing Sheets

Related U.S. Application Data

(60) Provisional application No. 62/856,549, filed on Jun. 3, 2019.

(56) References Cited

U.S. PATENT DOCUMENTS

| | | |
|---|---|---|
| 2018/0056068 A1 | 3/2018 | Zhang et al. |
| 2018/0085583 A1* | 3/2018 | Zhang ................ A61N 1/36071 |
| 2019/0269919 A1 | 9/2019 | Brill et al. |
| 2020/0376272 A1 | 12/2020 | Block et al. |

OTHER PUBLICATIONS

"U.S. Appl. No. 16/879,018, Notice of Allowance mailed Jan. 13, 2022", 8 pgs.

"U.S. Appl. No. 16/879,018, PTO Response to Rule 312 Communication mailed Feb. 11, 2022", 2 pgs.

Veizi, Elias, et al., "Spinal Cord Stimulation (SCS) with Anatomically Guided (3D) Neural Targeting Shows Superior Chronic Axial Low Back Pain Relief Compared to Traditional SCS-Lumina Study", Pain Medicine 2017; 0: 1-15, doi: 10.1093/pm/pnw286.

* cited by examiner

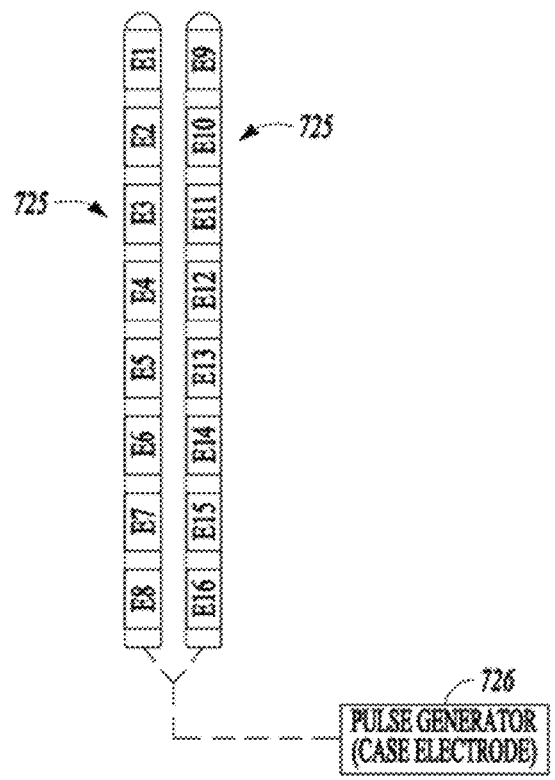
FIG. 7
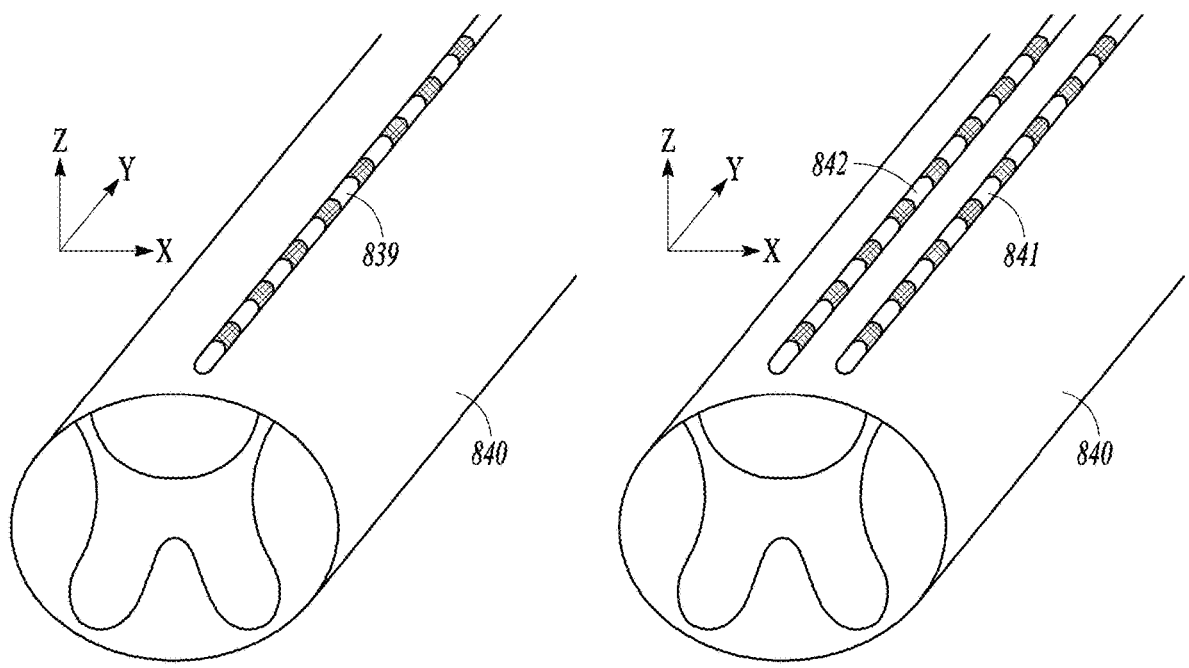
FIG. 8A
FIG. 8B

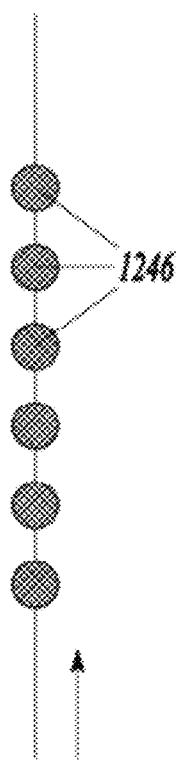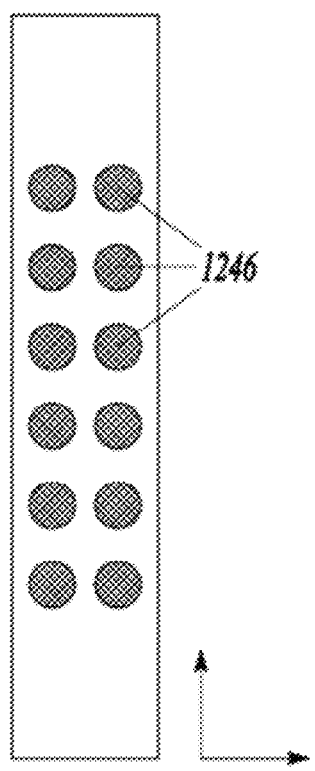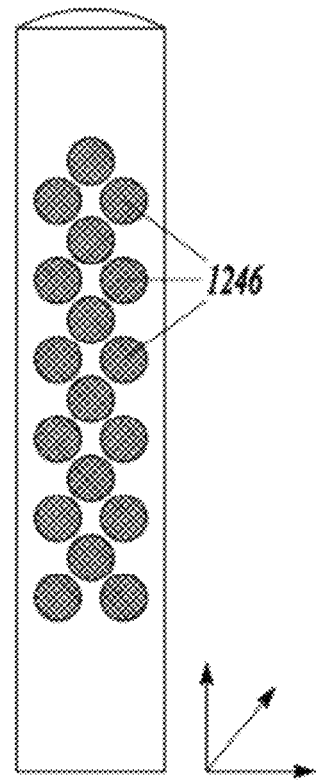
*FIG. 12A*　　*FIG. 12B*　　*FIG. 12C*

TARGETED ELECTROSTIMULATION FIELDS BASED ON FOCAL DERMATOMAL COVERAGE

CLAIM OF PRIORITY

This application is a continuation of U.S. patent application Ser. No. 16/879,018, filed on May 20, 2020, which claims the benefit of priority under 35 U.S.C. § 119(e) of U.S. Provisional Patent Application Ser. No. 62/856,549, filed on Jun. 3, 2019, which is herein incorporated by reference in its entirety.

TECHNICAL FIELD

This document relates generally to medical devices, and more particularly, to systems, devices and methods for delivering neuromodulation.

BACKGROUND

Neuromodulation (or "neural neuromodulation", also referred to as "neurostimulation" or "neural stimulation") has been proposed as a therapy for a number of conditions. Often, neuromodulation and neural stimulation may be used interchangeably to describe excitatory stimulation that causes action potentials as well as inhibitory and other effects. Examples of neuromodulation include Spinal Cord Stimulation (SCS), Deep Brain Stimulation (DBS), Peripheral Nerve Stimulation (PNS), and Functional Electrical Stimulation (FES). SCS, by way of example and not limitation, has been used to treat chronic pain syndromes.

Conventional SCS delivers electrical pulses to the dorsal column fibers in the dorsal aspect of the spinal cord, which in turn activate a set of inhibitory neurons in the dorsal horn, thereby masking the transmission of pain signals from the periphery of the body to the brain. Notably, the dorsal column fibers are organized in a spatially-dependent manner according to the region of the body with which they respectively interface. Accordingly, it is desirable to optimally target the neuromodulation to the precise fibers that correspond to the source of pain to be treated, while minimizing stimulation of other fibers in order to reduce or avoid side effects.

However, it can be a challenge to find a desirable or optimal location (sweet-spot) for the neuromodulation field during programming of a neuromodulation device. Optimal-location searching involves a healthcare professional adjusting the targeting of the neuromodulation to provide optimal pain relief for the patient with minimal discomfort. State-of-the-art systems provide the ability to create complex electrode configurations to create virtual poles by combining fractionalized current output from physical electrodes in the vicinity of the desired virtual pole. Though beneficial for targeting specific areas, the complexity of adjusting multiple virtual poles to provide optimal neuromodulation for the patient presents a number of problems including extended duration of testing, and the possibility of causing patient discomfort during testing. Complex neuroanatomy in certain spinal cord regions also increases the difficulty in finding an optimal neuromodulation field design and programming the neuromodulation device accordingly to achieve desired therapeutic effect of pain relief.

SUMMARY

The following examples illustrate various aspects of the embodiments described herein.

Example 1 is a system for controlling neuromodulation therapy for pain relief in a patient. The system comprising an electrostimulator, a data receiver, and a processor circuit. The electrostimulator can be configured to stimulate target tissue of the patient via a set of electrodes at respective electrode locations according to a stimulation setting to induce paresthesia. The data receiver can be configured to receive pain data including information of pain sites on a body of the patient, and to receive patient feedback on the induced paresthesia including information of paresthesia sites on the patient body. The processor circuit can be configured to: generate an indication of spatial correspondence between the pain sites and the paresthesia sites over one or more dermatomes; determine, for each of the electrode locations, an anodic weight and a cathodic weight using at least the spatial correspondence indication; and generate a stimulation field definition for neuromodulation pain therapy using the anodic and cathodic weights corresponding to one or more of the electrode locations.

In Example 2, the subject matter of Example 1 optionally includes the processor circuit that can include an electrode energy fractionalizer configured to generate a fractionalized electrode configuration based on the stimulation field definition, the fractionalized electrode configuration including individually regulated electrical current to individual ones of the set of electrodes; and the electrostimulator that can be configured to generate and apply sub-perception stimulation energy to the target tissue for pain relief via the set of electrodes in accordance with the individually regulated electrical current to the individual ones of the set of electrodes.

In Example 3, the subject matter of any one or more of Examples 1-2 optionally includes a stimulation controller configured to generate a control signal to: adjust a central point of stimulation (CPS) by trolling the CPS along a length of a spinal cord, the CPS representing a focal point of a stimulation field; and trigger electrostimulation of the target tissue to induce paresthesia according to the adjusted CPS.

In Example 4, the subject matter of Example 3 optionally includes the stimulation controller that can be further configured to generate a control signal for adjusting one or more stimulation parameters including: a stimulation pulse width; a stimulation amplitude; or a stimulation rate.

In Example 5, the subject matter of any one or more of Examples 1-4 optionally includes the pain data that can include a pain drawing of the pain sites, and the patent feedback that can include a paresthesia drawing of the paresthesia sites, and the processor circuit that can be configured to generate the spatial correspondence indication based on an overlapping area between the pain drawing and the paresthesia drawing across one or more dermatomes.

In Example 6, the subject matter of Example 5 optionally includes the processor circuit that can be configured to: pixelate the pain drawing into pixels corresponding to anatomical point locations of the pain sites; pixelate the paresthesia drawing into pixels corresponding to anatomical point locations of the paresthesia sites; and determine the overlapping area using the pixelated pain drawing and the pixelated paresthesia drawing.

In Example 7, the subject matter of any one or more of Examples 5-6 optionally includes the patient feedback that can further include a patient comfort indicator of the induced paresthesia. The processor circuit can be configured to determine or adjust the anodic weight and the cathodic weight using the patient comfort indicator.

In Example 8, the subject matter of Example 7 optionally includes the patient comfort indicator that can include a preference score or a side-effect score of the induced paresthesia, and the processor circuit that can be configured to: determine the cathodic weight proportional to a product of the preference score and the overlapping area; and determine the anodic weight proportional to a product of the side-effect score and an area of the paresthesia drawing excluding the overlapping area.

In Example 9, the subject matter of any one or more of Examples 1-8 optionally includes the processor circuit that can be configured to determine for each of the electrode locations a corresponding perception threshold of paresthesia, and to determine or adjust the anodic weight or the cathodic weight using the determined perception threshold.

In Example 10, the subject matter of Example 9 optionally includes the data receiver that can be configured to receive a patient physiological response to the induction of paresthesia, and the processor circuit that can be configured to determine the corresponding perception threshold for each of the electrode locations using the sensed a patient physiological response to the induction of paresthesia.

In Example 11, the subject matter of Example 10 optionally includes a sensor configured to sense the patient physiological response to the induction of paresthesia from one or more of the paresthesia sites, the sensor including one or more of: an electromyography (EMG) sensor; an electrospinogram (ESG) sensor; an electrically evoked compound action potential (eCAP) sensor; or a tissue impedance sensor.

In Example 12, the subject matter of any one or more of Examples 9-11 optionally includes the processor circuit that can be configured to determine for each of the electrode locations the corresponding perception threshold further using neuroanatomy information of target neural structures including one or more of: a trajectory or an entry pattern of one or more dorsal roots; or a spatial proximity indication of the electrode locations with respect to one or more dorsal roots.

In Example 13, the subject matter of any one or more of Examples 9-12 optionally includes\the processor circuit that can be configured to determine for each of the electrode locations the corresponding perception threshold further using a patient comfort indicator of the induced paresthesia.

In Example 14, the subject matter of any one or more of Examples 9-13 optionally includes the processor circuit that can be configured to determine for each of the electrode locations the corresponding perception threshold using a computational model.

In Example 15, the subject matter of any one or more of Examples 1-14 optionally includes the processor circuit that can be configured to determine the anodic weight and the cathodic weight using a machine-learning model.

Example 16 is a method for controlling neuromodulation therapy for pain relief in a patient. The method comprises step of: receiving pain data including information of pain sites on a body of the patient; stimulating target tissue of the patient via a set of electrodes at respective electrode locations according to a stimulation setting to induce paresthesia; receiving patient feedback on the induced paresthesia including information of paresthesia sites on the patient body; generating an indication of spatial correspondence between the pain sites and the paresthesia sites over one or more dermatomes; determining, for each of the electrode locations, an anodic weight and a cathodic weight using at least the spatial correspondence indication; and generating a stimulation field definition for neuromodulation pain therapy using the anodic and cathodic weights corresponding to one or more of the electrode locations.

In Example 17, the subject matter of Example 16 optionally includes steps of: determining a fractionalized electrode configuration based on the stimulation field definition, the fractionalized electrode configuration including individually regulated electrical current to individual ones of the set of electrodes; and generating and applying sub-perception stimulation energy to the target tissue for pain relief via the set of electrodes in accordance with the fractionalized electrode configuration.

In Example 18, the subject matter of any one or more of Examples 16-17 optionally includes stimulating target tissue to induce paresthesia, which can include steps of: adjusting a central point of stimulation (CPS) by trolling the CPS along a length of a spinal cord, the CPS representing a focal point of a stimulation field; and delivering electrostimulation of the target tissue to induce paresthesia according to the adjusted CPS.

In Example 19, the subject matter of any one or more of Examples 16-18 optionally includes the pain data that can include a pain drawing of the pain sites, and the patent feedback that can include a paresthesia drawing of the paresthesia sites, and the step of generating the spatial correspondence indication can include determining an overlapping area between the pain drawing and the paresthesia drawing across one or more dermatomes.

In Example 20, the subject matter of Example 19 optionally includes the patient feedback that can further include a patient comfort indicator indicating patient preference or side-effect of the induced paresthesia. The anodic weight and the cathodic weight can be determined or adjusted by using the patient comfort indicator.

In Example 21, the subject matter of any one or more of Examples 16-20 optionally includes determining, for each of the electrode locations, a corresponding perception threshold of paresthesia, and wherein the anodic weight and the cathodic weight can be determined or adjusted by using the determined perception threshold.

In Example 22, the subject matter of Example 21 optionally includes determining the corresponding perception threshold of paresthesia based on one or more of: a sensor signal indicative of patient physiological response to the induction of paresthesia; neuroanatomy information of target neural structures; or a patient comfort indicator of the induced paresthesia.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 7 illustrates, by way of example, some features of the neuromodulation leads and a pulse generator.

FIGS. 8A-8B are schematic views of embodiments of neuromodulation lead placement on a patient's spinal cord.

FIGS. 12A-12C illustrate, by way of example and not limitation, neural tissue locations that may be targeted within the test region in one, two and three dimensions, respectively.

DETAILED DESCRIPTION

Figure 1:
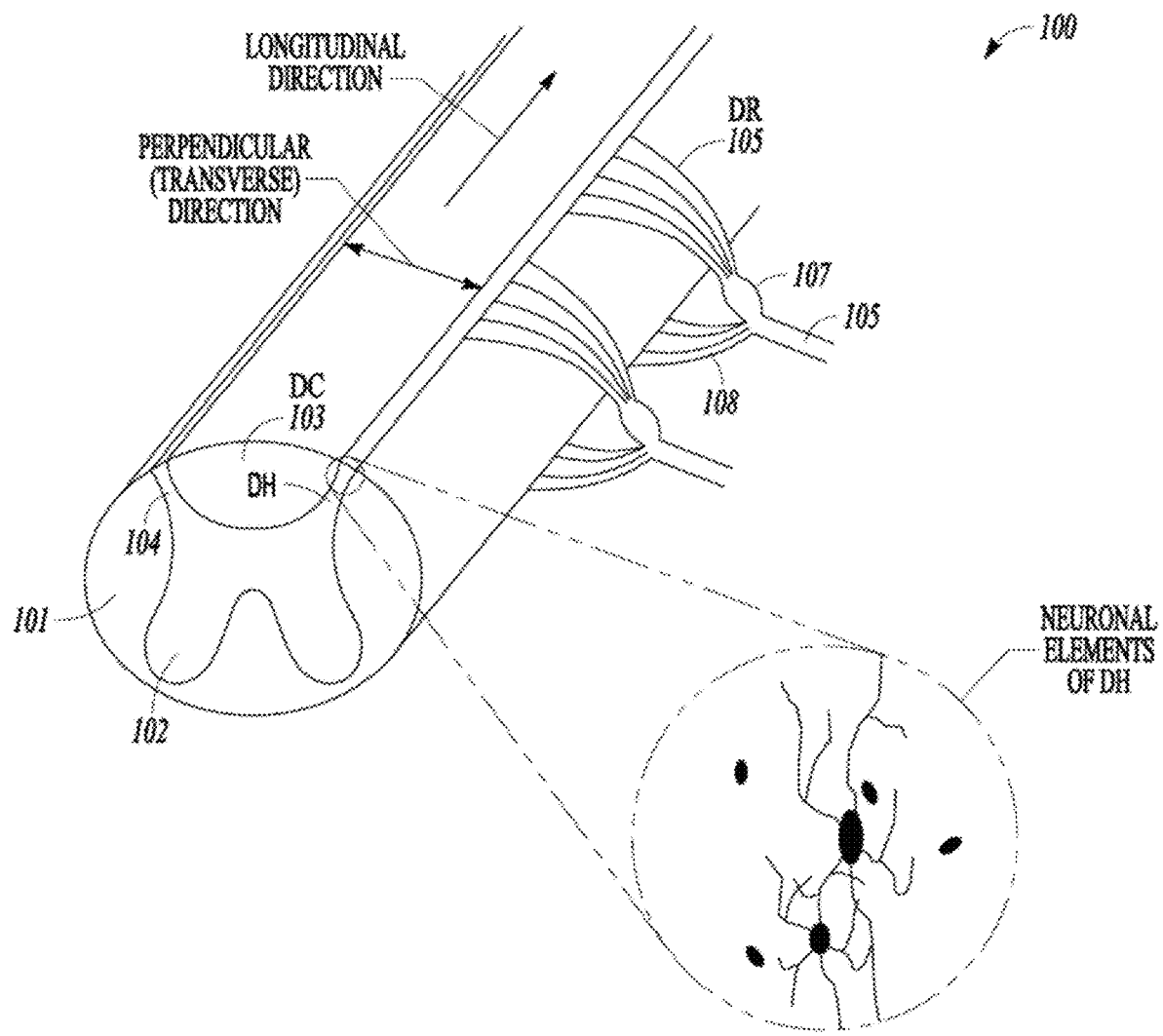
FIG. 1 illustrates a portion of a spinal cord.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Various embodiments described herein involve neuromodulation of target tissue such as a portion of a spinal cord to relieve pain. The neuromodulation may include sub-perception stimulation therapeutically effective but non-perceptible (apart from any therapeutic effects) to the patient. Thus, the therapeutic effects of the sub-perception neuromodulation can be perceived by the patient.

The complex spinal cord structure resides in a complex three-dimensional environment. For example, the thickness of the cerebrospinal fluid (CSF), which is between the spinal cord and the epidural space, varies along the spine. Thus, the distance between the spinal cord and one or more neuromodulation leads within the epidural space likely varies. Furthermore, neither the leads nor the spinal cord form simple straight lines. The positions of implanted neuromodulation leads can also vary and are not perfectly parallel to the spinal cord. Additionally, the neuroanatomy of the spinal cord region can vary from patient to patient. It is desirable to program a modulation system to account for electrode positions and variations in conductance through the electrodes and tissue to improve therapy programming.

Various embodiments of the present subject matter provide systems and methods for facilitating the creation of a target neuromodulation field with improved precision using a dermatomal coverage of pain area, patient information such as feedback on the induced paresthesia, and paresthesia perception thresholds at different body sites (e.g., dermatomes). The dermatomal coverage may be represented by a spatial correspondence between patient body sites of pain perception and patient body sites of paresthesia over one or more dermatomal compartments. The patient information may include a preference score or a side-effect score representing patient comfort level regarding the induced paresthesia. The paresthesia perception thresholds may be determined using neurophysiological information sensed by a sensor. According to various embodiments, a neuromodulation system may determine, for each of a plurality of electrode locations, an anodic weight and a cathodic weight using one or more of the dermatomal coverage, the patient information, or the paresthesia perception thresholds. The system may generate a stimulation field definition using the anodic and cathodic weights corresponding to different electrode locations. The stimulation field definition includes parameters such as field size, shape, and intensity, and field scaling and steering parameters. Based on the stimulation field definition, the processor circuit may individually regulate electrical energy to individual electrodes that collectively stimulate the target tissue for pain relief. Various embodiments described herein may help ease the burden of programming a neuromodulation system, such as a spinal cord stimulation (SCS) system for pain relief, particularly in a spinal cord region with complex anatomical structures, such as lumber dorsal roots of a spinal cord.

As some embodiments described herein involve SCS (also referred to as spinal cord neuromodulation), a brief description of the physiology of the spinal cord is provided herein to assist the reader. FIG. 1 illustrates, by way of example, a portion of a spinal cord 100 including white matter 101 and gray matter 102 of the spinal cord. The gray matter 102 includes cell bodies, synapse, dendrites, and axon terminals. Thus, synapses are located in the gray matter. White matter 101 includes myelinated axons that connect gray matter areas. A typical transverse section of the spinal cord includes a central "butterfly" shaped central area of gray matter 102 substantially surrounded by an ellipse-shaped outer area of white matter 101. The white matter of the dorsal column (DC) 103 includes mostly large myelinated axons that form afferent fibers that run in an axial direction. The dorsal portions of the "butterfly" shaped central area of gray matter are referred to as dorsal horns (DH) 104. In contrast to the DC fibers that run in an axial direction, DH fibers can be oriented in many directions, including perpendicular to the longitudinal axis of the spinal cord. Examples of spinal nerves 105 are also illustrated, including a dorsal root (DR) 105, dorsal root ganglion 107 and ventral root 108. The dorsal root 105 mostly carries sensory signals into the spinal cord, and the ventral root functions as an efferent motor root. The dorsal and ventral roots join to form mixed spinal nerves 105.

SCS has been used to alleviate pain. A therapeutic goal for conventional SCS programming has been to maximize stimulation (i.e., recruitment) of the DC fibers that run in the white matter along the longitudinal axis of the spinal cord and minimal stimulation of other fibers that run perpendicular to the longitudinal axis of the spinal cord (dorsal root fibers, predominantly), as illustrated in FIG. 1. The white matter of the DC includes mostly large myelinated axons that form afferent fibers. While the full mechanisms of pain relief are not well understood, it is believed that the perception of pain signals is inhibited via the gate control theory of pain, which suggests that enhanced activity of innocuous touch or pressure afferents via electrical stimulation creates interneuronal activity within the DH of the spinal cord that releases inhibitory neurotransmitters (Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, the large sensory afferents of the DC nerve fibers have been targeted for stimulation at an amplitude that provides pain relief. Current implantable neuromodulation systems typically include electrodes implanted adjacent, i.e., resting near, or upon the dura, to the dorsal column of the spinal cord of the patient and along a longitudinal axis of the spinal cord of the patient.

Activation of large sensory DC nerve fibers also typically creates the paresthesia sensation that often accompanies conventional SCS therapy. Although alternative or artifactual sensations, such as paresthesia, are usually tolerated relative to the sensation of pain, patients sometimes report these sensations to be uncomfortable, and therefore, they can be considered an adverse side-effect to neuromodulation therapy in some cases. Some embodiments discussed herein deliver sub-perception therapy that is therapeutically effective to treat pain, for example. However, the patient does not sense the delivery of the neuromodulation field (e.g. paresthesia) during a sub-perception therapy. Sub-perception therapy may be provided using higher frequency neuromodulation (e.g. about 1500 Hz or above) of the spinal cord. Sub-perception neuromodulation may also be provided through neuromodulation field shaping (e.g., using multiple independent current control, or MICC), and temporal shaping of pulse train (e.g., burst, longer pulses). It appears that these higher frequencies may effectively block the transmission of pain signals in the afferent fibers in the DC. Some embodiments herein selectively modulate DH tissue or DR tissue over DC tissue to provide sub-perception therapy.

Such selective neuromodulation may be delivered at lower frequencies. For example, the selective neuromodulation may be delivered at frequencies less than 1,200 Hz. The selective neuromodulation may be delivered at frequencies less than 1,000 Hz in some embodiments. In some embodiments, the selective neuromodulation may be delivered at frequencies less than 500 Hz. In some embodiments, the selective neuromodulation may be delivered at frequencies less than 350 Hz. In some embodiments, the selective neuromodulation may be delivered at frequencies less than 130 Hz. The selective neuromodulation may be delivered at low frequencies (e.g. as low as 2 Hz). The selective neuromodulation may be delivered even without pulses (e.g. 0 Hz) to modulate some neural tissue. By way of example and not limitation, the selective neuromodulation may be delivered within a frequency range selected from the following frequency ranges: 2 Hz to 1,200 Hz; 2 Hz to 1,000 Hz, 2 Hz to 500 Hz; 2 Hz to 350 Hz; or 2 Hz to 130 Hz. Systems may be developed to raise the lower end of any these ranges from 2 Hz to other frequencies such as, by way of example and not limitation, 10 Hz, 20 Hz, 50 Hz or 100 Hz.

The selective neuromodulation may be delivered with a duty cycle, in which stimulation (e.g. a train of pulses) is delivered during a Stimulation ON portion of the duty cycle, and is not delivered during a Stimulation OFF portion of the duty cycle. The selected modulation may be delivered with fixed or variable pulse widths. By way of example and not limitation, the duty cycle may be about 10%±5%, 20%±5%, 30%±5%, 40%±5%, 50%±5% or 60%±5%. For example, a burst of pulses for 10 ms during a Stimulation ON portion followed by 15 ms without pulses corresponds to a 40% duty cycle.

It is to be noted that while SCS is specifically discussed as a neuromodulation therapy, such discussion is by way of example and not limitation. Various embodiments can also include applying the priming techniques including timing of delivery discussed in this document to Peripheral Nerve Stimulation (PNS) therapies. For example, sub-perception PNS may be applied to alleviate pain. Various embodiments include priming the neural tissue at target locations for delivering the neuromodulation where required intensity of the neuromodulation for testing and/or therapeutic purposes may be lowered.

Figure 2:
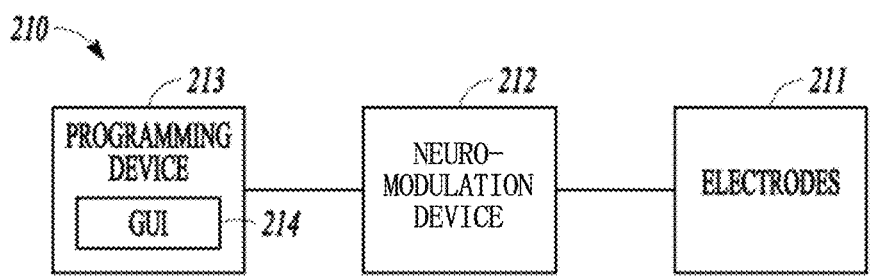
FIG. 2 illustrates, by way of example, an embodiment of a neuromodulation system.

FIG. 2 illustrates an embodiment of a neuromodulation system 210, which includes electrodes 211, a neuromodulation device 212, and a programming device 213. The electrodes 211 are configured to be placed on or near one or more neural targets in a patient. The electrodes 211 may form part of an electrode arrangement. The neuromodulation device 212 is configured to be electrically connected to electrodes 211 and deliver neuromodulation energy, such as in the form of electrical pulses, to the one or more neural targets though electrodes 211. The delivery of the neuromodulation is controlled using a plurality of neuromodulation parameters, such as neuromodulation parameters specifying the electrical pulses and a selection of electrodes through which each of the electrical pulses is delivered. In various embodiments, at least some parameters of the plurality of neuromodulation parameters are programmable, either manually by a user (e.g., physician or other caregiver) or at least partially automatically in a closed-loop neuromodulation system. The programming device 213 may provide the user with accessibility to the user-programmable parameters. In various embodiments, the programming device 213 is configured to be communicatively coupled to neuromodulation device via a wired or wireless link. In various embodiments, the programming device 213 includes a graphical user interface (GUI) 214 that allows the user to set and/or adjust values of the user-programmable neuromodulation parameters.

In various embodiments, the neuromodulation system 210 can include implantable and external elements. For example, the neuromodulation device 212 can be an implantable neuromodulation device, the electrodes 211 can include electrodes in one or more implantable lead and/or the implantable neuromodulation device, and the programming device can be an external programming device configured to be communicatively coupled to the implantable neuromodulation device via telemetry, as further discussed with reference to FIGS. 5 and 6. In another example, the neuromodulation device 212 can be an external neuromodulation device such as a Transcutaneous Electrical Neural Stimulation (TENS) device, the electrodes 211 can include surface electrodes such as skin patch electrodes, and the programming device can be an external programming device configured to be communicatively coupled to the implantable neuromodulation device via a wired or wireless link, or integrated with the external neuromodulation device. In still another example, the neuromodulation device 212 can be an external neuromodulation device, the electrodes 211 can include percutaneous electrodes, and the programming device can be an external programming device configured to be communicatively coupled to the implantable neuromodulation device via a wired or wireless link, or integrated with the external neuromodulation device. In various embodiments, an external neuromodulation device with surface and/or percutaneous electrodes can be used, for example, for delivering a test neuromodulation, delivering a therapeutic neuromodulation during a trial period, and delivering a short-term therapeutic neuromodulation.

In one embodiment, an external neuromodulation device with surface electrodes can be used during a trial period prior to a potential implantation of an implantable SCS system. A skin patch including the surface electrodes is placed over the patient's spine near the region where percutaneous electrodes will be placed for use during the trial period. The external neuromodulation device such as a dedicated External Trial Stimulator (ETC) and/or an external TENS device may be used to deliver stimulation energy to induce paresthesia and mapping dermatomal coverage of the pain sensation using one or more electrodes selected from the surface electrodes. The external neuromodulation device may also be programmed to deliver therapeutic neuromodulation (e.g., sub-threshold neuromodulation) through the percutaneous electrodes immediately following the placement of the percutaneous electrodes.

Figure 3:
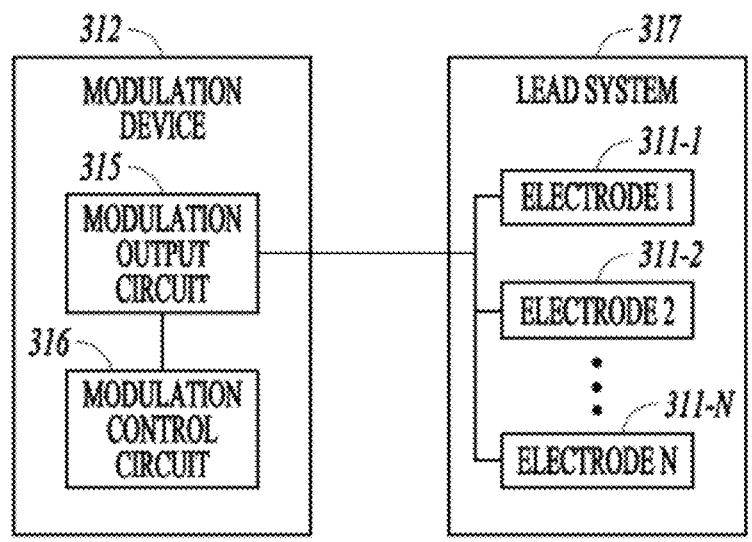
FIG. 3 illustrates, by way of example, an embodiment of a neuromodulation device, such as may be implemented in the neuromodulation system of FIG. 2.

FIG. 3 illustrates an embodiment of a neuromodulation device 312, such as may be implemented in the neuromodulation system 210 of FIG. 2. The illustrated embodiment of the neuromodulation device 312 includes a neuromodulation output circuit 315 and a neuromodulation control circuit 316. Those of ordinary skill in the art will understand that the neuromodulation device 312 may include additional components such as sensing circuitry for patient monitoring and/or feedback control of the therapy, telemetry circuitry and power. The neuromodulation output circuit 315 produces and delivers neuromodulation pulses. The neuromodulation control circuit 316 controls the delivery of the neuromodulation pulses using the plurality of neuromodulation parameters. The combination of the neuromodulation output circuit 315 and neuromodulation control circuit 316 may collectively be referred to as a pulse generator. The lead system 317 includes one or more leads each configured to be electrically connected to neuromodulation device 312 and a plurality of electrodes 311-1 to 311-N (where N≥2) distributed in an electrode arrangement using the one or more leads. Each lead may have an electrode array consisting of two or more electrodes, which also may be referred to as contacts. Multiple leads may provide multiple electrode arrays to provide the electrode arrangement. Each electrode is a single electrically conductive contact providing for an electrical interface between neuromodulation output circuit 315 and tissue of the patient. The neuromodulation pulses are each delivered from the neuromodulation output circuit 315 through a set of electrodes selected from the electrodes 311-1 to 311-N. The number of leads and the number of electrodes on each lead may depend on, for example, the distribution of target(s) of the neuromodulation and the need for controlling the distribution of electric field at each target. In one embodiment, by way of example and not limitation, the lead system includes two leads each having eight electrodes. Some embodiments may use a lead system that includes one or more leads of the same or different types such as percutaneous leads, linear paddles, multiple-column paddles, or directional leads, among others.

The neuromodulation system may be configured to modulate spinal target tissue or other neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. An electrical waveform may be controlled or varied for delivery using electrode configuration(s). The electrical waveforms may be analog or digital signals. In some embodiments, the electrical waveform includes pulses. The pulses may be delivered in a regular, repeating pattern, or may be delivered using complex patterns of pulses that appear to be irregular. Other parameters that may be controlled or varied include the amplitude, pulse width, and rate (or frequency) of the electrical pulses. Each electrode configuration, along with the electrical pulse parameters, can be referred to as a "neuromodulation parameter set." Each set of neuromodulation parameters, including fractionalized current distribution to the electrodes (as percentage cathodic current, percentage anodic current, or off), may be stored and combined into a neuromodulation program that can then be used to modulate multiple regions within the patient.

The number of electrodes available combined with the ability to generate a variety of complex electrical pulses, presents a huge selection of neuromodulation parameter sets to the clinician or patient. For example, if the neuromodulation system to be programmed has sixteen electrodes, millions of neuromodulation parameter sets may be available for programming into the neuromodulation system. Furthermore, for example SCS systems may have thirty-two electrodes which exponentially increases the number of neuromodulation parameters sets available for programming. To facilitate such selection, the clinician generally programs the neuromodulation parameters sets through a computerized programming system to allow the optimum neuromodulation parameters to be determined based on patient feedback or other means and to subsequently program the desired neuromodulation parameter sets.

Patient paresthesia perception may be used to program SCS therapy, such as by selecting or determining an appropriate neuromodulation parameter set. The paresthesia induced by neuromodulation and perceived by the patient may be located in approximately the same places of the patient body where pain is sensed and thus the target site of treatment. Conventionally, when leads are implanted within the patient, an operating room (OR) mapping procedure may be performed to apply neuromodulation to test placement of the leads and/or electrodes, thereby assuring that the leads and/or electrodes are implanted in effective locations within the patient.

Once the leads are correctly positioned, a fitting procedure, which may be referred to as a navigation session, may be performed to program the external control device, and if applicable the neuromodulation device, with a set of neuromodulation parameters that best addresses the painful site. Thus, the navigation session may be used to pinpoint the volume of activation (VOA) or areas correlating to the pain. The procedure may be implemented to target the tissue during implantation, or after implantation should the leads gradually or unexpectedly move that would otherwise relocate the neuromodulation energy away from the target site. By reprogramming the neuromodulation device (typically by independently varying the neuromodulation energy on the electrodes), the VOA can often be moved back to the effective pain site without having to re-operate on the patient in order to reposition the lead and its electrode array. According to various embodiments discussed in this document, in addition to the information of dermatomal coverage such as correspondence between body sites of pain and body sites of induced paresthesia, one or more of patient information such as feedback on the induced paresthesia or patient perception thresholds may be used to optimize the target neuromodulation field. This may not only improve the neuromodulation precision and thus better therapeutic outcome, but may also save a system operator's time and ease the burden of programming a neuromodulation system.

Figure 4:
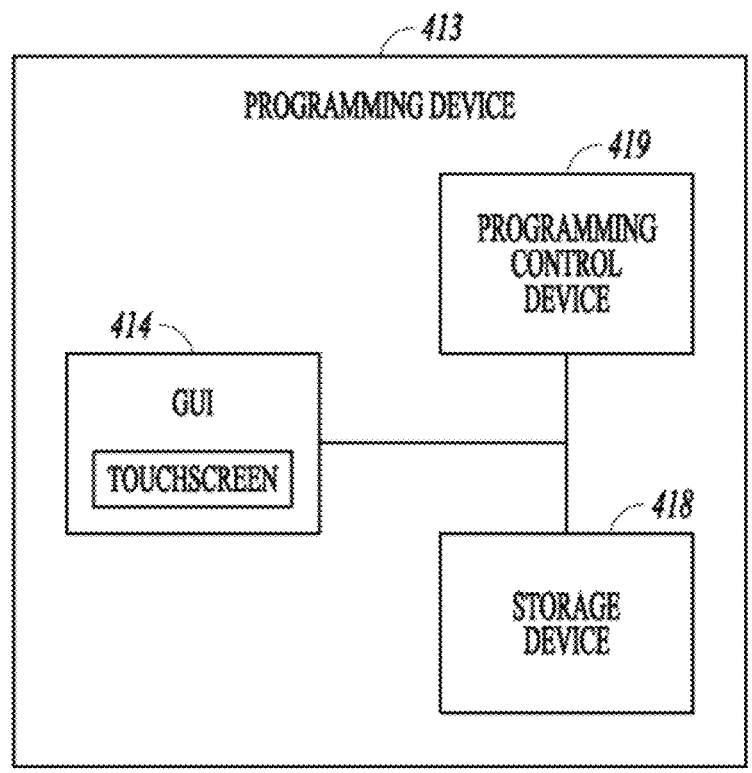
FIG. 4 illustrates, by way of example, an embodiment of a programming device, such as may be implemented as the programming device in the neuromodulation system of FIG. 2.

FIG. 4 illustrates an embodiment of a programming device 413, such as may be implemented as the programming device 213 in the neuromodulation system of FIG. 2. The programming device 413 includes a storage device 418, a programming control circuit 419, and a GUI 414. The programming control circuit 419 generates the plurality of neuromodulation parameters that controls the delivery of the neuromodulation pulses according to the pattern of the neuromodulation pulses. In various embodiments, the GUI 414 includes any type of presentation device, such as interactive or non-interactive screens, and any type of user input devices that allow the user to program the neuromodulation parameters, such as touchscreen, keyboard, keypad, touchpad, trackball, joystick, and mouse. The storage device 418 may store, among other things, neuromodulation parameters to be programmed into the neuromodulation device. The programming device 413 may transmit the plurality of neuromodulation parameters to the neuromodulation device. In some embodiments, the programming device 413 may transmit power to the neuromodulation device. The programming control circuit 419 may generate the plurality of neuromodulation parameters. In various embodiments, the programming control circuit 419 may check values of the plurality of neuromodulation parameters against safety rules to limit these values within constraints of the safety rules.

In various embodiments, circuits of neuromodulation, including its various embodiments discussed in this document, may be implemented using a combination of hardware, software and firmware. For example, the circuit of a GUI, neuromodulation control circuit, and programming control circuit, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 5:
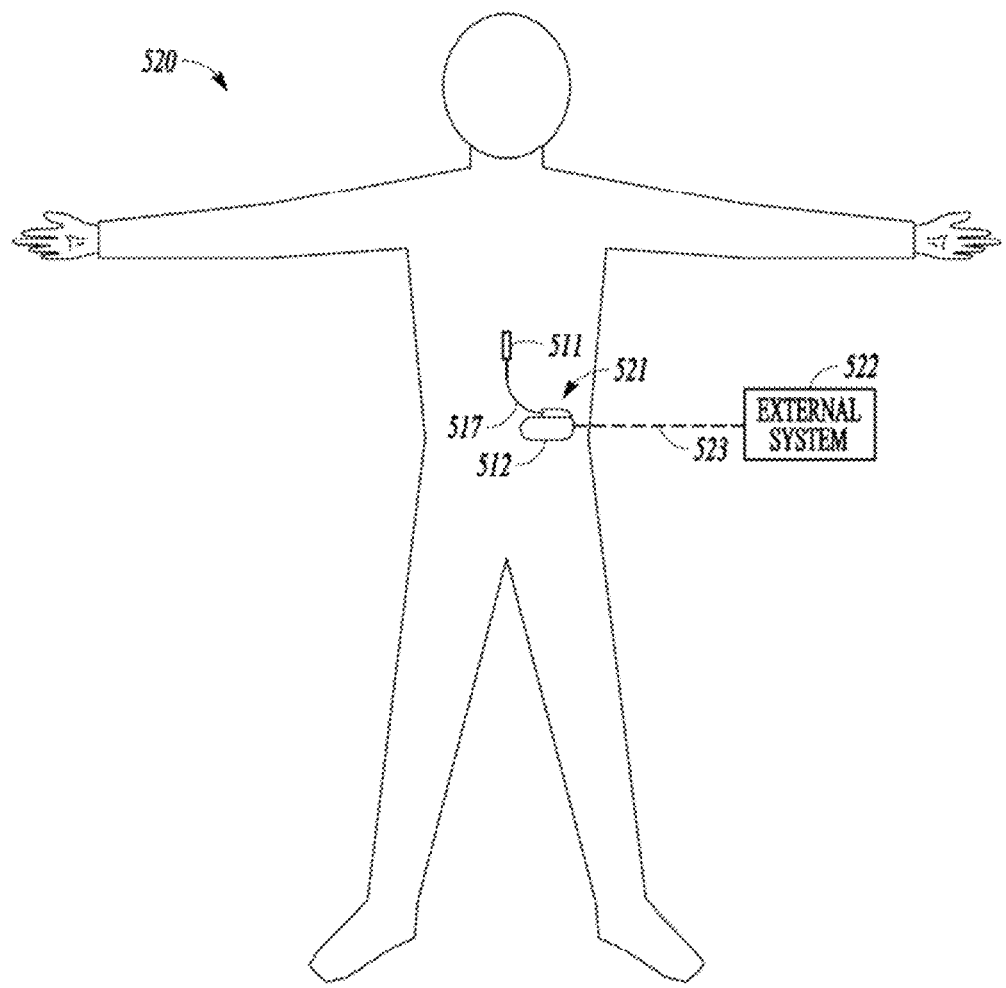
FIG. 5 illustrates, by way of example, an implantable neuromodulation system and portions of an environment in which system may be used.

FIG. 5 illustrates, by way of example, an implantable neuromodulation system and portions of an environment in which system may be used. The system is illustrated for implantation near the spinal cord. However, neuromodulation system may be configured to modulate other neural targets such as may be useful for delivering other therapies. The system 520 includes an implantable system 521, an external system 522, and a telemetry link 523 providing for wireless communication between implantable system 521 and external system 522. The implantable system is illustrated as being implanted in the patient's body. The implantable system 521 includes an implantable neuromodulation device (also referred to as an implantable pulse generator, or IPG) 512, a lead system 517, and electrodes 511. The lead system 517 includes one or more leads each configured to be electrically connected to the neuromodulation device 512 and a plurality of electrodes 511 distributed in the one or more leads. In various embodiments, the external system 402 includes one or more external (non-implantable) devices each allowing a user (e.g. a clinician or other caregiver and/or the patient) to communicate with the implantable system 521. In some embodiments, the external system 522 includes a programming device intended for a clinician or other caregiver to initialize and adjust settings for the implantable system 521 and a remote control device intended for use by the patient. For example, the remote control device may allow the patient to turn a therapy on and off and/or adjust certain patient-programmable parameters of the plurality of neuromodulation parameters.

The neuromodulation lead(s) of the lead system 517 may be placed adjacent, i.e., resting near, or upon the dura, adjacent to the spinal cord area to be stimulated. For example, the neuromodulation lead(s) may be implanted along a longitudinal axis of the spinal cord of the patient. Due to the lack of space near the location where the neuromodulation lead(s) exit the spinal column, the implantable neuromodulation device 512 may be implanted in a surgically-made pocket either in the abdomen or above the buttocks, or may be implanted in other locations of the patient's body. The lead extension(s) may be used to facilitate the implantation of the implantable neuromodulation device 512 away from the exit point of the neuromodulation lead(s).

Figure 6:
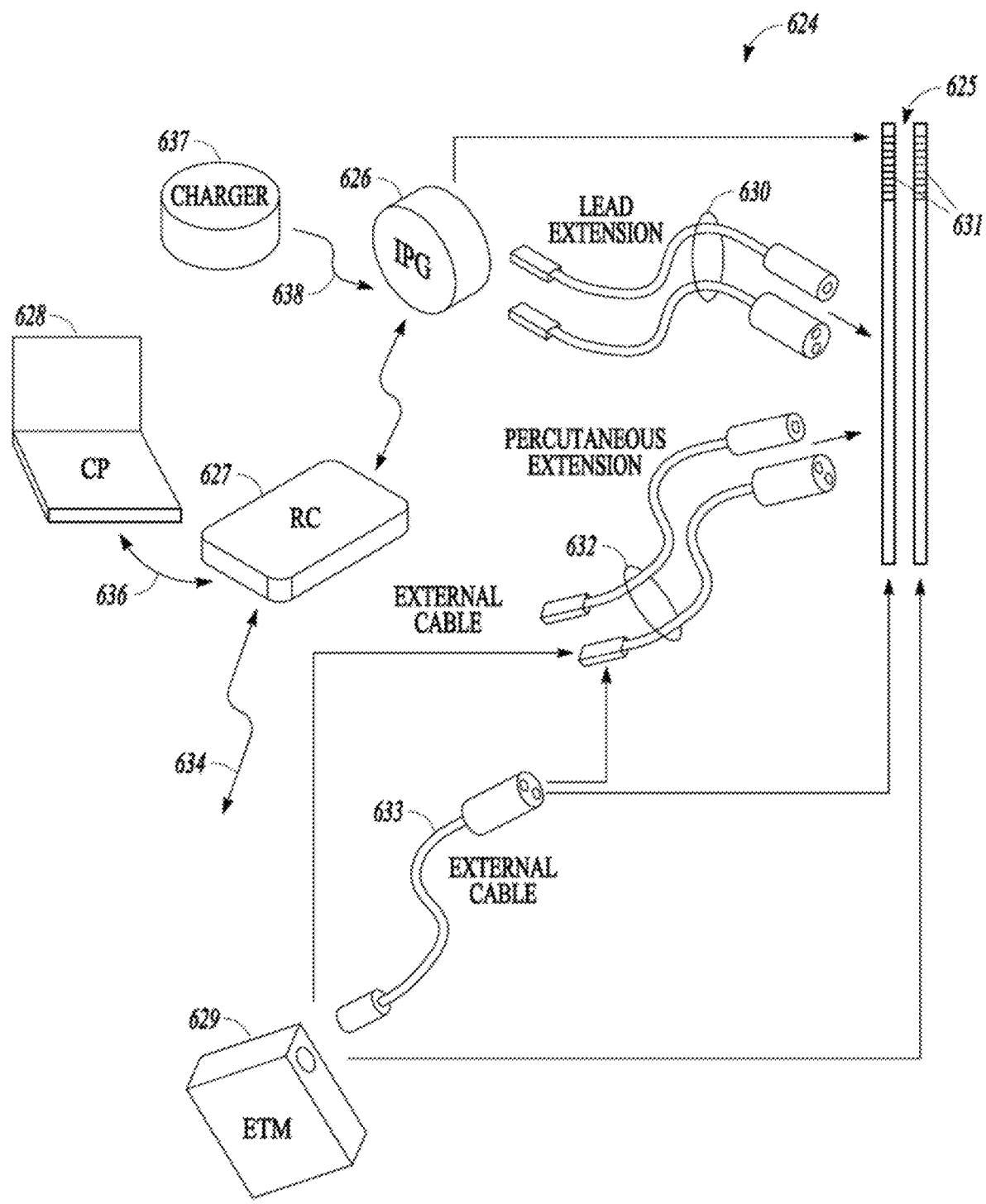
FIG. 6 illustrates, by way of example, an embodiment of a Spinal Cord Stimulation (SCS) system, which also may be referred to as a Spinal Cord Neuromodulation (SCM) system.

FIG. 6 illustrates, by way of example, an embodiment of a SCS system, which also may be referred to as a Spinal Cord Neuromodulation (SCM) system. The SCS system 624 may generally include a plurality (illustrated as two) of implantable neuromodulation leads 625, an implantable pulse generator (IPG) 626, an external remote controller RC 627, a clinician's programmer (CP) 628, and an external trial modulator (ETM) 629. The IPG 626 may be physically connected via one or more percutaneous lead extensions 630 to the neuromodulation leads 625, which carry a plurality of electrodes 631. As illustrated, the neuromodulation leads 625 may be percutaneous leads with the electrodes arranged in-line along the neuromodulation leads. Any suitable number of neuromodulation leads can be provided, including only one, as long as the number of electrodes is greater than two (including the IPG case function as a case electrode) to allow for lateral steering of the current. Alternatively, a surgical paddle lead can be used in place of one or more of the percutaneous leads. The IPG 626 includes pulse generation circuitry, also referred to as a pulse generator, that delivers electrical neuromodulation energy in the form of a pulsed electrical waveform (i.e., a temporal series of electrical pulses) to the electrodes in accordance with a set of neuromodulation parameters.

The ETM 629 may also be physically connected via the percutaneous lead extensions 632 and external cable 633 to the neuromodulation leads 625. The ETM 629 may have similar pulse generation circuitry as the IPG 626 to deliver electrical neuromodulation energy to the electrodes accordance with a set of neuromodulation parameters. The ETM 629 is a non-implantable device that is used on a trial basis after the neuromodulation leads 625 have been implanted and prior to implantation of the IPG 626, to test the responsiveness of the neuromodulation that is to be provided. Functions described herein with respect to the IPG 626 can likewise be performed with respect to the ETM 629.

The RC 627 may be used to telemetrically control the ETM 629 via a bi-directional RF communications link 634. The RC 627 may be used to telemetrically control the IPG 626 via a bi-directional RF communications link 635. Such control allows the IPG 626 to be turned on or off and to be programmed with different neuromodulation parameter sets. The IPG 626 may also be operated to modify the programmed neuromodulation parameters to actively control the characteristics of the electrical neuromodulation energy output by the IPG 626. A clinician may use the CP 628 to program neuromodulation parameters into the IPG 626 and ETM 629 in the operating room and in follow-up sessions.

The CP 628 may indirectly communicate with the IPG 626 or ETM 629, through the RC 627, via an IR communications link 636 or other link. The CP 628 may directly communicate with the IPG 626 or ETM 629 via an RF communications link or other link (not shown). The clinician detailed neuromodulation parameters provided by the CP 628 may also be used to program the RC 627, so that the neuromodulation parameters can be subsequently modified by operation of the RC 627 in a stand-alone mode (i.e., without the assistance of the CP 628). Various devices may function as the CP 628. Such devices may include portable devices such as a lap-top personal computer, mini-computer, personal digital assistant (PDA), tablets, phones, or a remote control (RC) with expanded functionality. Thus, the programming methodologies can be performed by executing software instructions contained within the CP 628. Alternatively, such programming methodologies can be performed using firmware or hardware. In any event, the CP 628 may actively control the characteristics of the electrical neuromodulation generated by the IPG 626 to allow the desired parameters to be determined based on patient feedback or other feedback and for subsequently programming the IPG 626 with the desired neuromodulation parameters. To allow the user to perform these functions, the CP 628 may include a user input device (e.g., a mouse and a keyboard), and a programming display screen housed in a case. In addition to, or in lieu of, the mouse, other directional programming devices may be used, such as a trackball, touchpad, joystick, touch screens or directional keys included as part of the keys associated with the keyboard. An external device (e.g. CP) may be programmed to provide display screen(s) that allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical neuromodulation energy output by the neuromodulation leads, and select and program the IPG with neuromodulation parameters in a surgical or clinical setting.

An external charger 637 may be a portable device used to transcutaneously charge the IPG via a wireless link such as an inductive link 638. Once the IPG has been programmed, and its power source has been charged by the external charger or otherwise replenished, the IPG may function as programmed without the RC or CP being present.

FIG. 7 illustrates, by way of example, some features of the neuromodulation leads 725 and a pulse generator 726. The pulse generator 726 may be an implantable device (IPG) or may be an external device such as may be used to test the electrodes during an implantation procedure. In the illustrated example, one of the neuromodulation leads has eight electrodes (labeled E1-E8), and the other neuromodulation lead has eight electrodes (labeled E9-E16). The actual number and shape of leads and electrodes may vary for the intended application. An implantable pulse generator (IPG) may include an outer case for housing the electronic and other components. The outer case may be composed of an electrically conductive, biocompatible material, such as titanium, that forms a hermetically-sealed compartment wherein the internal electronics are protected from the body tissue and fluids. In some cases, the outer case may serve as an electrode (e.g. case electrode). The IPG may include electronic components, such as a controller/processor (e.g., a microcontroller), memory, a battery, telemetry circuitry, monitoring circuitry, neuromodulation output circuitry, and other suitable components known to those skilled in the art. The microcontroller executes a suitable program stored in memory, for directing and controlling the neuromodulation performed by IPG.

Electrical neuromodulation energy is provided to the electrodes in accordance with a set of neuromodulation parameters programmed into the pulse generator. The electrical neuromodulation energy may be in the form of a pulsed electrical waveform. Such neuromodulation parameters may comprise electrode combinations, which define the electrodes that are activated as anodes (positive), cathodes (negative), and turned off (zero), percentage of neuromodulation energy assigned to each electrode (fractionalized electrode configurations), and electrical pulse parameters, which define the pulse amplitude (measured in milliamps or volts depending on whether the pulse generator supplies constant current or constant voltage to the electrode array), pulse width (measured in microseconds), pulse rate (measured in pulses per second), and burst rate (measured as the neuromodulation on duration X and neuromodulation off duration Y). The electrical pulse parameters may define an intermittent neuromodulation with "ON" periods of time where a train of two or more pulses are delivered and "OFF" periods of time where pulses are not delivered. Electrodes that are selected to transmit or receive electrical energy are referred to herein as "activated," while electrodes that are not selected to transmit or receive electrical energy are referred to herein as "non-activated."

Electrical neuromodulation occurs between or among a plurality of activated electrodes, one of which may be the IPG case. The system may be capable of transmitting neuromodulation energy to the tissue in a monopolar or multipolar (e.g., bipolar, tripolar, etc.) fashion. Monopolar neuromodulation occurs when a selected one of the lead electrodes is activated along with the case of the IPG, so that neuromodulation energy is transmitted between the selected electrode and case. Any of the electrodes E1-E16 and the case electrode may be assigned to up to k possible groups or timing "channels." In one embodiment, k may equal four. The timing channel identifies which electrodes are selected to synchronously source or sink current to create an electric field in the tissue to be stimulated. Amplitudes and polarities of electrodes on a channel may vary. In particular, the electrodes can be selected to be positive (anode, sourcing current), negative (cathode, sinking current), or off (no current) polarity in any of the k timing channels. The IPG may be operated in a mode to deliver electrical neuromodulation energy that is therapeutically effective and causes the patient to perceive delivery of the energy (e.g. therapeutically effective to relieve pain with perceived paresthesia), and may be operated in a sub-perception mode to deliver electrical neuromodulation energy that is therapeutically effective and does not cause the patient to perceive delivery of the energy (e.g. therapeutically effective to relieve pain without perceived paresthesia).

The IPG may be configured to individually control the electrical current flowing through each of the electrodes. For example, a current generator may be configured to selectively generate individual current-regulated amplitudes from independent current sources for each electrode. In some embodiments, the pulse generator may have voltage regulated outputs. While individually programmable electrode amplitudes are desirable to achieve fine control, a single output source switched across electrodes may also be used, although with less fine control in programming. Neuromodulators may be designed with mixed current and voltage regulated devices.

FIGS. 8A-8B are schematic views of embodiments of neuromodulation lead placement on a patient's spinal cord. Specifically, FIG. 8A is a schematic view of a single electrical neuromodulation lead 839 implanted over approximately the longitudinal midline of the spinal cord 840. It is understood that additional leads or lead paddle(s) may be used, such as may be used to provide a wider electrode arrangement and/or to provide the electrodes closer to dorsal horn elements, and that these electrode arrays also may implement fractionalized current. FIG. 8B illustrates an embodiment where two electrical neuromodulation leads are implanted near the spinal cord. A first electrical neuromodulation lead 841 is implanted more laterally with respect to the spinal cord, thereby placing it proximate the dorsal horn of the spinal cord. A second electrical neuromodulation lead 842 is implanted more medially with respect to the spinal cord, thereby placing it proximate the dorsal column of the spinal cord 840.

Placement of the lead more proximal to the DH than the DC may be desirable to preferentially stimulate DH elements over DC neural elements for a sub-perception therapy. Lead placement may also enable preferential neuromodulation of dorsal roots over other neural elements. Any other plurality of leads or a multiple column paddle lead can also be used. Longitudinal component of the electrical field is directed along the y-axis depicted in each of FIGS. 8A-8B, and a transverse component of the electrical field is directed along the x-axis depicted in each of FIGS. 8A-8B. Some embodiments may include directional leads with one or more directional electrodes. A directional electrode may extend less than 360 degrees about the circumference of a lead body. For example, a row of two or more directional electrodes (e.g. "segmented electrodes") may be positioned along the circumference of the lead body. Activating select ones of the segmented electrodes may help extend and shape the field in a preferred direction.

Figure 9A:
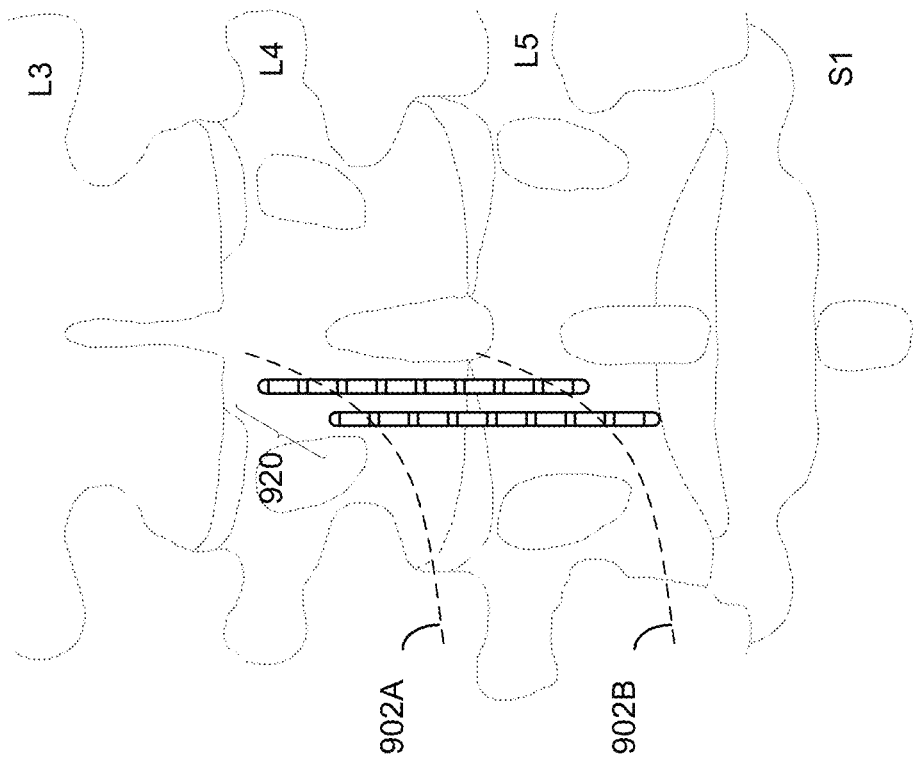
FIGS. 9A-9E are schematic views of embodiments of neuromodulation lead placement on caudal regions of spinal column for stimulating dorsal root fibers.
Figure 9B:
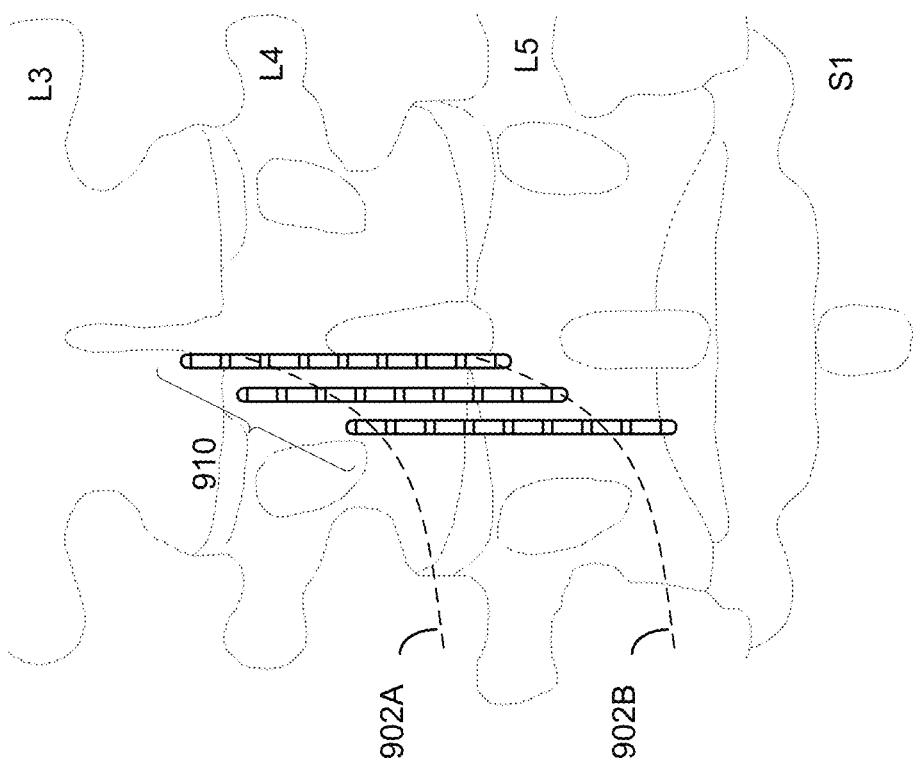
Figure 9C:
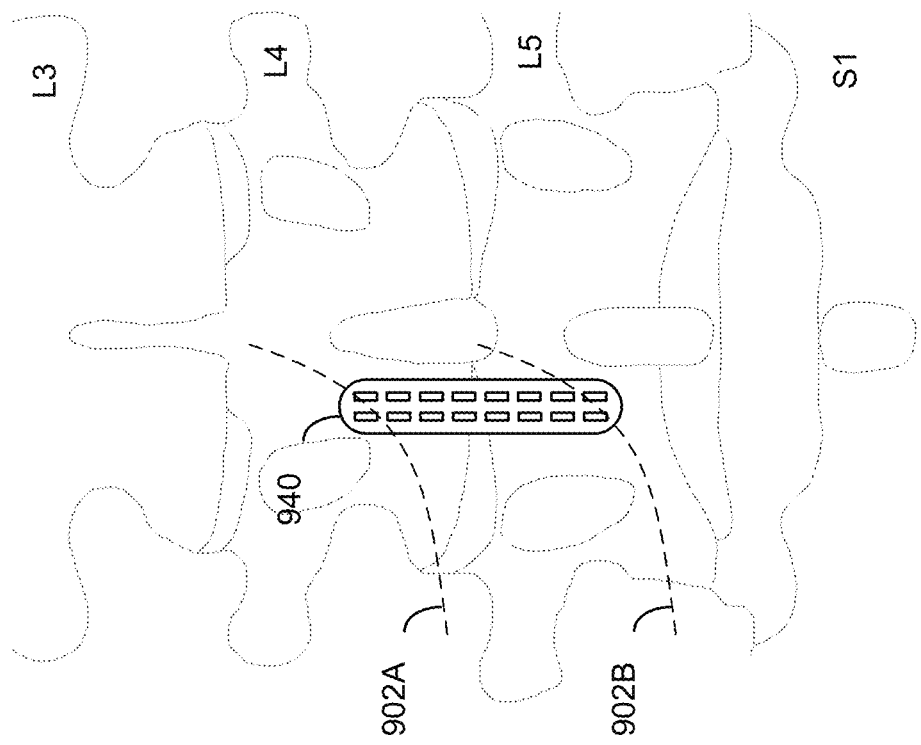
Figure 9D:
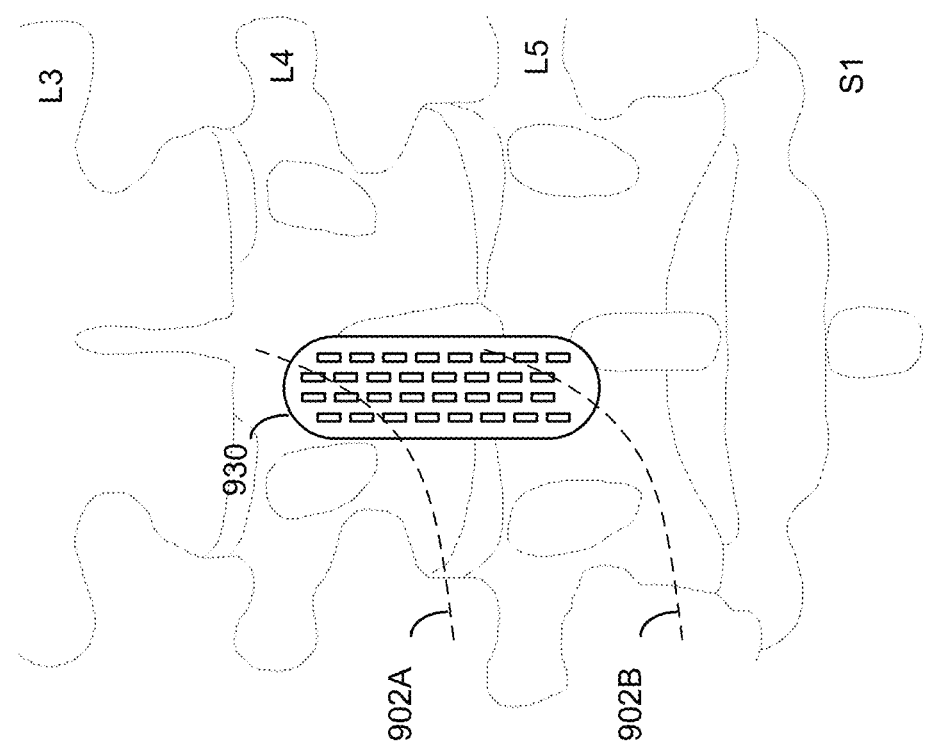
Figure 9E:
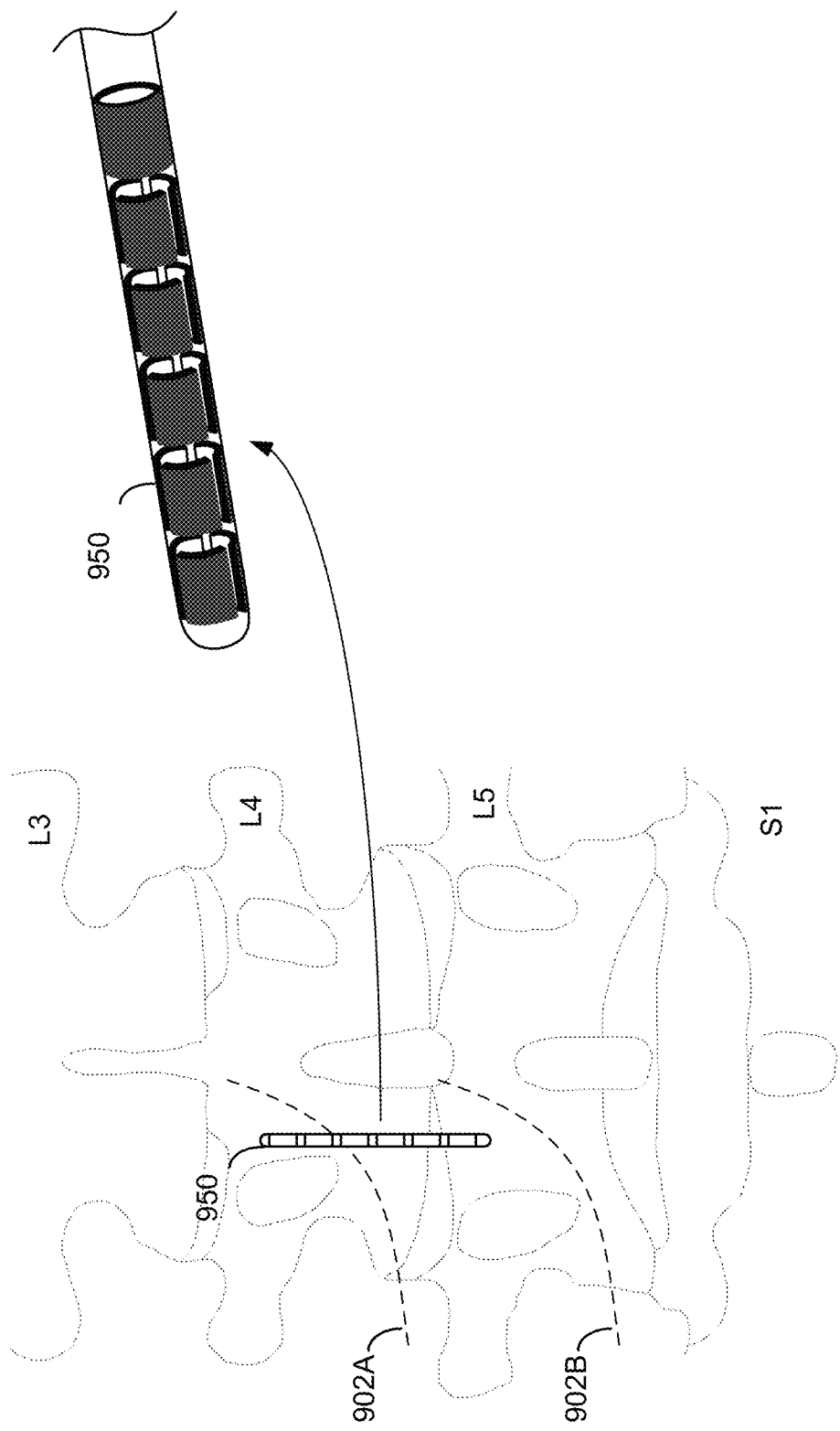

It is to be understood that additional neuromodulation leads or paddle(s) of the same or different types may be used, such as may be used to provide a wider electrode arrangement and/or to provide the electrodes closer to dorsal horn elements. In some examples, the neuromodulation leads or paddles may be placed at regions more caudal to the end of the spinal cord, and the electrode arrays on the neuromodulation lead also may implement fractionalized current. FIGS. 9A-9E are schematic views of embodiments of neuromodulation lead placement on caudal regions of spinal column, such as the level of L3-L5 and S1, where virtually no spinal cord, but only dorsal roots, among other neural structures, are present. The neuromodulation leads or paddles may be placed medial or lateral to the spinal column, and proximal to one or more dorsal roots, and are configured to deliver modulation energy to the dorsal root fibers. In FIG. 9A, three percutaneous leads 910 are positioned toward the left side of the spinal canal, and in FIG. 9B two percutaneous leads 920 are positioned toward the left side of the spinal canal. In FIG. 9C, a single four-column paddle lead 930 is positioned toward the left side of the spinal canal, and in FIG. 9D, a single two-column paddle lead 940 is positioned toward the left side of the spinal canal. In FIG. 9E, a single percutaneous lead 950 is positioned toward the left side of the spinal canal. In the illustrated example, the percutaneous lead 950 includes multiple segmented electrodes that enable lateral control of the stimulation location via a single lead. Moreover, because the segmented electrodes are placed in close lateral proximity, they can be used to provide a high degree of lateral stimulation resolution.

While the examples illustrated in FIGS. 9A-9E show electrode lead placements to the left side of the spinal canal, these are by way of example and not limitation. In any of FIGS. 9A-9E, lead placements to the right side of the spinal canal may also be utilized. As can be seen from the figures, different types of leads with different numbers of electrodes and different electrode spacing (including different types than those shown) may be employed to provide dorsal root stimulation. These example lead placements differ from the placement of leads more proximal to the anatomical midline in traditional spinal cord stimulation (SCS) therapy.

The dorsal root trajectories 902A and 902B in FIGS. 9A-9E show that dorsal root fibers have different trajectories from dorsal column fibers, and they are not aligned with the anatomical midline. Accordingly, relative locations (e.g., lead entry angles) between the lead and the neural targets (e.g., dorsal column fibers or dorsal root fibers) can vary at different anatomical regions, as shown in FIGS. 8A-8B and FIGS. 9A-9E. When neuromodulation is specifically being targeted to dorsal root fibers, it is desirable to know the locations of the dorsal roots such that stimulation can be customized. The present document describes various embodiments of incorporating anatomy information of target neural tissue (e.g., trajectory of dorsal roots) and patient feedback to paresthesia into the process of stimulation field design, which may help improve the neuromodulation precision and thus better therapeutic outcome such as pain relief.

Figure 10:
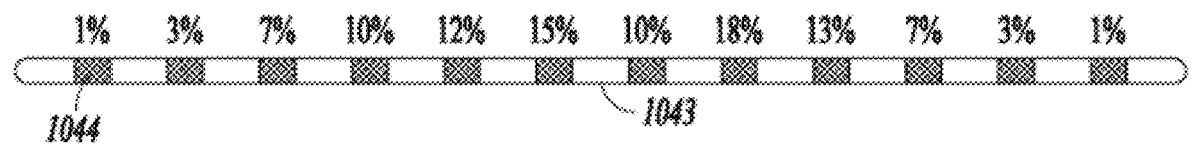
FIG. 10 illustrates a schematic view of the electrical neuromodulation lead showing an example of the fractionalization of the anodic current delivered to the electrodes on the electrical neuromodulation lead.

FIG. 10 is a schematic view of an electrical neuromodulation lead 1043 showing an example of the fractionalization of the anodic current delivered to the electrodes on the electrical neuromodulation lead. These figures illustrate fractionalization using monopolar neuromodulation where a case electrode of the IPG is the only cathode, and carries 100% of the cathodic current. The fractionalization of the anodic current shown in FIG. 10 does not deliver an equal amount of current to each electrode 1044, because this embodiment takes into account electrode/tissue coupling differences, which are the differences in how the tissue underlying each electrode reacts to electrical neuromodulation. Also, the ends of the portion of the electrical neuromodulation lead include electrodes having lower gradient in the longitudinal direction. The magnitude of the electrical field tapers down at the ends of the electrical neuromodulation lead. Fractionalization of the current may accommodate variation in the tissue underlying those electrodes. The fractionalization across the electrical neuromodulation lead can vary in any manner as long as the total of fractionalized currents equals 100%. Various embodiments described herein implement a programmed algorithm to determine the appropriate fractionalization to achieve a desired neuromodulation field property.

Neuromodulation thresholds vary from patient to patient and from electrode to electrode within a patient. An electrode/tissue coupling calibration of the electrodes may be performed to account for these different neuromodulation thresholds and provide a more accurate fractionalization of the current between electrodes. For example, perception threshold may be used to normalize the electrodes. The RC or the CP may be configured to prompt the patient to actuate a control element, once paresthesia is perceived by the patient. In response to this user input, the RC or the CP may be configured to respond to the user input by storing the neuromodulation signal strength when the control element is actuated. Other sensed parameter or patient-perceived neuromodulation values (e.g. constant paresthesia, or maximum tolerable paresthesia) may be used to provide the electrode/tissue coupling calibration of the electrodes.

The SCS system may be configured to deliver different electrical fields to achieve a temporal summation of neuromodulation. The electrical fields can be generated respectively on a pulse-by-pulse basis. For example, a first electrical field can be generated by the electrodes (using a first current fractionalization) during a first electrical pulse of the pulsed waveform, a second different electrical field can be generated by the electrodes (using a second different current fractionalization) during a second electrical pulse of the pulsed waveform, a third different electrical field can be generated by the electrodes (using a third different current fractionalization) during a third electrical pulse of the pulsed waveform, a fourth different electrical field can be generated by the electrodes (using a fourth different current fractionalized) during a fourth electrical pulse of the pulsed waveform, and so forth. These electrical fields may be rotated or cycled through multiple times under a timing scheme, where each field is implemented using a timing channel. The electrical fields may be generated at a continuous pulse rate, or may be bursted on and off. Furthermore, the interpulse interval (i.e., the time between adjacent pulses), pulse amplitude, and pulse duration during the electrical field cycles may be uniform or may vary within the electrical field cycle.

Some embodiments are configured to determine a neuromodulation parameter set to create a stimulation field definition to reduce or minimize neuromodulation of non-targeted tissue (e.g. DC tissue). The neuromodulation field may be shaped by using multiple independent current control (MICC) or multiple independent voltage control to guide the estimate of current fractionalization among multiple electrodes and estimate a total amplitude that provide a desired strength. For example, the neuromodulation field may be shaped to enhance the neuromodulation of DH neural tissue and to minimize the neuromodulation of DC tissue. A benefit of MICC is that MICC accounts for various in electrode-tissue coupling efficiency and perception threshold at each individual contact, so that "hot-spot" stimulation is eliminated.

Figures 11A, 11B:
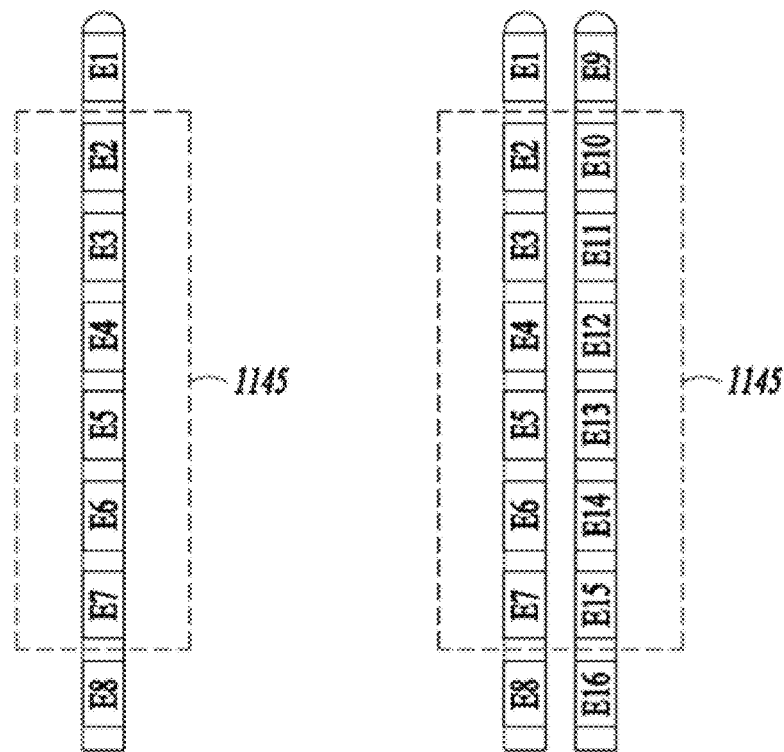
FIGS. 11A-11B illustrate, by way of example and not limitation, electrode arrangements and test regions of neural tissue along the electrode arrangements.

FIGS. 11A-11B illustrate, by way of example and not limitation, electrode arrangements (e.g. E1-E8 in FIG. 11A and E1-E16 in FIG. 11B) and test regions 1145 of neural tissue along the electrode arrangements. These test regions 1145 may extend across the entire electrode arrangement. In some embodiments, the test regions may extend along only a portion of the electrode arrangement. By way of example, some embodiments may allow a user to select the test region and thus select the portion of the electrode arrangement to be tested. In the example illustrated in FIG. 11A the test region is neural tissue along the E2 to E7 electrodes, and in the example illustrated in FIG. 11B the test region is neural tissue along the E2 through E7 and the E10 to E15 electrodes.

The electrodes in the electrode arrangement may be fractionalized, using different neuromodulation parameter sets, to change the portion of the neural tissue that is modulated. Thus, there may be many neural tissue locations that can be targeted with the test region of neural tissue adjacent to the electrode arrangement. FIGS. 12A-12C illustrate, by way of example and not limitation, neural tissue locations 1246 that may be targeted within the test region in one, two and three dimensions, respectively. In the one-dimensional example illustrated in FIG. 12A, the neural locations that may be targeted may simply be a line of potential targets such as may be observed from a single lead with a linear arrangement of electrodes. In the two dimensional example illustrated in FIG. 12B the neural locations that may be targeted may be considered to lie in a plane proximate to the electrode arrangement. In the three-dimensional example illustrated in FIG. 12C, the neural locations that may be targeted may be considered to be a volume of tissue proximate to the electrode arrangement. By way of example, the two-dimensional and three-dimensional test regions may be implemented using two or more leads of electrodes. Thus, the test regions may be relatively simple or complex shapes, and may include relatively few or relatively many locations to be tested.

Figure 13:
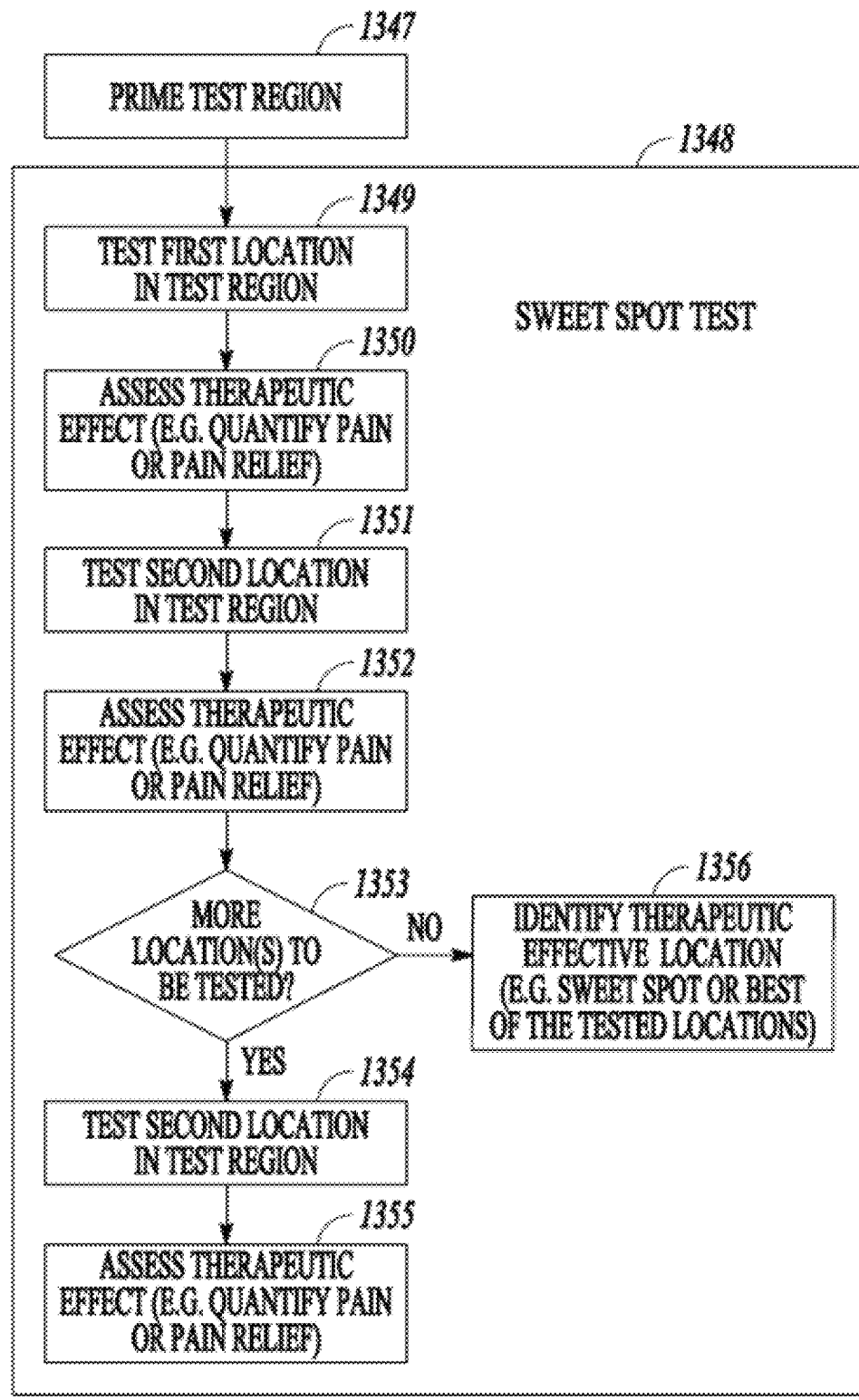
FIG. 13 illustrates an example of a method for finding a sweet spot for sub-perception neuromodulation.

FIG. 13 illustrates an example of a method 1300 for finding a sweet spot for sub-perception neuromodulation. In the illustrated example, a test region is primed with the sub-perception neuromodulation field 1347, and the sweet-spot test is performed 1348 to find location of neural tissue that is therapeutically effective when targeted with sub-perception neuromodulation. The sweet spot test may involve a manual process to reprogram the neuromodulation field parameter set with different values to change the targeted location of the neuromodulation field. In some embodiments of the test, the targeted location is automatically changed (e.g. trolled) by automatically changing values of the neuromodulation field parameter set. Some embodiments may semi-automatically change values of the neuromodulation field parameter set to change the targeted location of the neuromodulation field.

At 1349, a first location in the test region is tested by focusing the neuromodulation field onto the first location. At 1350, the therapeutic effect of modulating the first location is assessed. In an example where the therapy is a therapy to alleviate pain, the patient may provide this assessment by quantifying a level of pain or level of pain relief that they are experiencing. In some examples, a biomarker is used to provide an assessment of the therapeutic efficacy of the neuromodulation field focused on the tested location. At 1351, the neuromodulation field parameter set is changed to change the focus of the neuromodulation field to test a second location in the test region. At 1352, the therapeutic effect of modulating the second location is assessed. If more location(s) are to be tested, as illustrated at 1353, the process may continue to 1354 to test the next location. The process can then proceed to 2355 to assess the therapeutic effect of the next location. The process may determine or identify the location(s) that are therapeutically effective 1356 by evaluating the quantified effects of the therapy. In some embodiments, the quantified effects may be compared to each other to identify the tested location that has the best therapeutic effect or one of the best therapeutic effects.

The method 1300 may be performed to test relatively small locations using a more narrowly focused neuromodulation field such as generally illustrated above in FIGS. 12A-12C, or may be used to test relatively larger locations of neural tissue using a more uniform (less focused) neuromodulation field. The test of larger locations may be followed by a more focused test or tests within one of the larger location. In an example, a test may begin with full-lead then use a search algorithm to reduce the span and improve energy efficiency. This can be done from the RC or CP, or in the IPG with RC feedback. The proposed algorithms may rely on some form of feedback indicating the effectiveness of the neuromodulation. For example, a patient may provide feedback regarding pain relief. Feedback may also provide a biomarker signal. In another example, the test may include a step of confirming that the neuromodulation along the full lead is effective, then focusing the neuromodulation along a portion of the lead. Thus, for example, a generally uniform neuromodulation field may be provided along this smaller portion of the lead. This field is still broad as it may be provided across an area with multiple electrode contacts, but it is less than the entire electrode arrangement using electrode array(s) on the lead(s).

Figure 14:
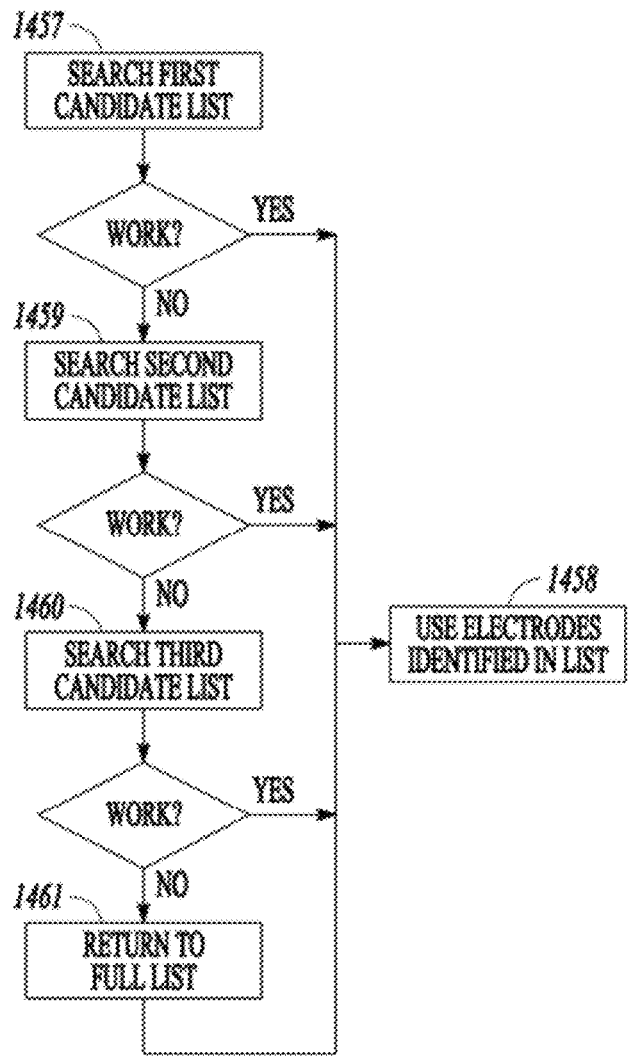
FIG. 14 illustrates, by way of example, aspects of a binary search routine as a rostrocaudal focus routine.

FIG. 14 illustrates, by way of example, aspects of a binary search routine as a rostrocaudal focus routine. A first subset of electrodes that define a first partial lead search region can be tested to determine if the neuromodulation is effective using the first subset 1457. If it is effective, the first subset of electrodes that define the first partial lead search region may be used to deliver the neuromodulation 1458 or for further more focused tests. If it is not effective, then a second subset of electrodes that define a second partial lead search region may be tested to determine if the second subset of electrodes is effective 1459. If it is effective, the second subset of electrodes that define the second partial lead search region may be used to deliver the neuromodulation 1458. If it is not effective, then a third (or nth) subset of electrodes that define a third (or nth) partial lead search region may be tested to determine if the third (or nth) subset of electrodes is effective 1460. If it is effective, the third (or nth) subset of electrodes that define the third (or nth) partial lead search region may be used to deliver the neuromodulation 1458. If it is not effective, then the binary search process may return to the full list of electrodes 1461 which was previously determined to be effective. At least some of the subsets of electrodes may be exclusive of each other. At least some of the subsets of electrodes may intersect with each other. In some embodiments, at least two subsets are exclusive, and at least one subset has an intersection with another subset.

Figure 15:
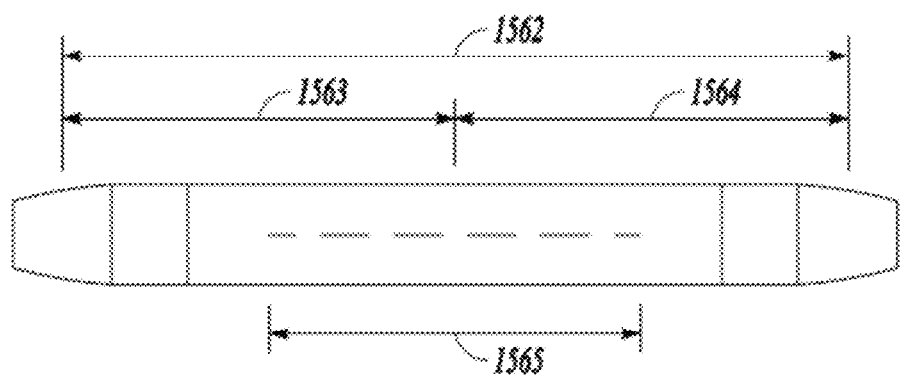
FIG. 15 illustrates an example of the binary search routine.

FIG. 15 illustrates an example of the binary search routine. The lead has a full span 1562 which may be split into three partial lead search regions 1563, 1564 and 1565, each partial search region including a corresponding subset of electrodes. By way of example and not limitation, the first and second subsets 1563 and 1564 of electrodes may be mutually exclusive, and third subset 1565 may include an intersection with the first subset and also may include an intersection with the second set. In an example, the full lead may be bifurcated to provide the first partial lead search region 1563 on a first side of the lead (e.g. left end of electrode array to middle) and the second partial lead search region 1564 on a second side of the lead (e.g. right end of the electrode array to middle). The third partial lead search region 1565 may partially overlap each of the first and second partial lead search regions. Thus, the partial lead search regions may define a first end region, a second end region and a middle region of the lead.

Figure 16A:
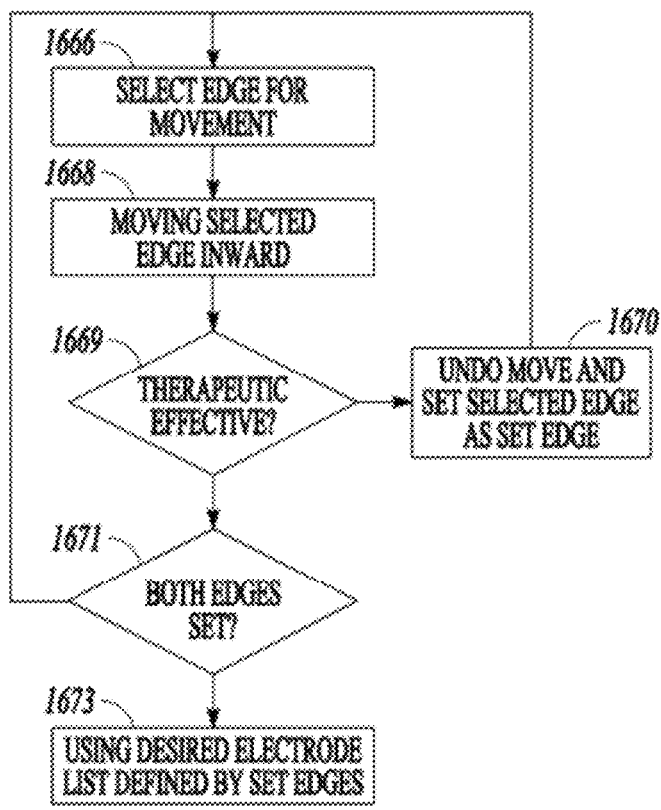
FIGS. 16A-16C illustrate, by way of example, an edge search routine.
Figure 16B:
Figure 16C:
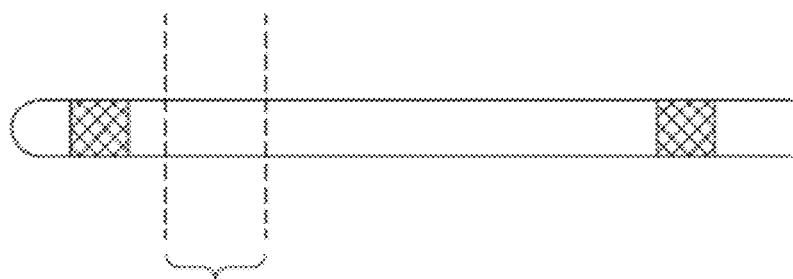

FIGS. 16A-16C illustrate, by way of example, an edge search routine. The edge search routine progressively moves each edge of the active electrodes in the array toward the middle and confirms that the neuromodulation remains effective with the moves. Thus, a first edge can be moved toward the center until the next move toward the center causes the neuromodulation to be ineffective; and a second edge can be moved toward the center until the next move toward the center causes the neuromodulation to be ineffective.

For example, the edge search routine may include selecting an edge of the electrode arrangement (e.g. array) for movement 1666. The selected edge may be one of the two edges 1667A or 1667B illustrated in FIG. 16B. However, there can be more than two edges if more than two regions are being focused. The selected edge is moved inward 1668 toward the other edge for the region of interest. If the reduced set of electrodes is no longer therapeutically effective 1669, then the previous move can be undone and that edge can be set so that is no longer is capable of being selected for movement 1670. The process can return to 1666 to attempt to move the other edge(s). If the reduced set of electrodes continues to be therapeutically effective 1669, then the process returns to 1666 to continue moving edges until such time as all of the edges are set 1671. The final reduced set 1672 of electrodes can be used 1673 to deliver the neuromodulation energy.

According to various embodiments, the programmed system may be configured with a neuromodulation focus routine such as a rostrocaudal focus routine to allow a user to select the desired electrodes for the neuromodulation to be more specific to the desired physiological area. Some embodiments may allow non-contiguous spans to be selected as a result of initial programming and/or neuromodulation refinement later on.

The neuromodulation field may be moved from location to location using an automatic trolling process or through patient control. Candidate trolling algorithms include a monopolar troll (e.g., anodic trolling or cathodic trolling) or a bipolar troll or a multipolar troll. The troll can be done with MICC or multiple independent voltage control, or with a timing channel interleaving technique. MICC enables the locus of the neuromodulation to be gradually moved across along the lead or within the array of electrodes. The interleaving of timing channels allows different electrode(s) in different timing channels. Values of stimulation parameter(s) (e.g. amplitude) in the timing channels can be adjusted. Thus by way of example and not limitation, if a monopolar neuromodulation is delivered using a first electrode in a first channel and another monopolar neuromodulation is delivered using a second electrode adjacent to the first electrode in a second channel, then the amplitude of the monopolar neuromodulation in the first channel may be incrementally reduced as the amplitude of the monopolar neuromodulation may be increase in the second channel. In this matter, the locus of the neuromodulation may be gradually adjusted.

Various embodiments troll a neuromodulation field, using an arrangement of electrodes on at least one lead, through neural tissue positions, and perform a quantification procedure multiple times as the neuromodulation field is trolled through the positions. The quantification procedure identifies when the neuromodulation field provides a therapeutic effect (e.g. pain relief). The quantification procedure may include receiving a marking signal that indicates that a neuromodulation intensity achieved the therapeutic effect, and storing a value for the therapeutic effect as well as neuromodulation field parameter data. The neuromodulation intensity may include neuromodulation parameters that affect the patient's perception of the neuromodulation energy. These parameters may include pulse width, rate, amplitude, distribution of current, and electrode polarity (cathode v. anode). By way of example and not limitation, the storage of the parameter data may be in a temporary storage such as but not limited to cache or RAM or in permanent/persistent storage such as but not limited to ROM, a memory device such a hard drive, optical disc, thumb drive, or cloud storage. The quantification process may include receiving a titration signal that indicates an instruction to adjust neuromodulation intensity, and adjusting the neuromodulation intensity in response to receiving the titration signal. The titration signal may be initiated by a patient, or by a clinician or other user who is responding to patient responses.

Figure 17:
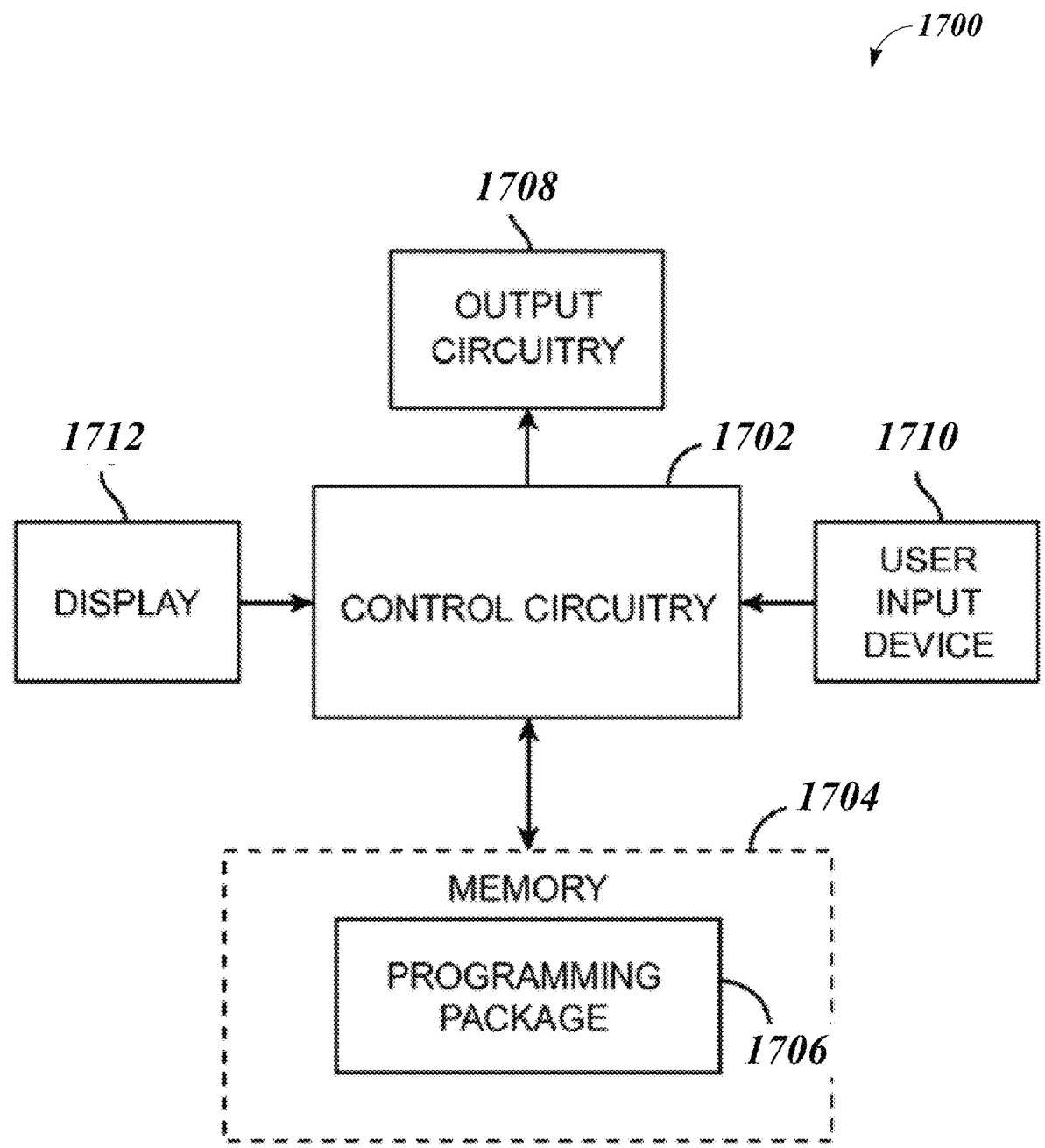
FIG. 17 is a diagram illustrating a programming device in greater detail according to an embodiment.

FIG. 17 is a diagram 1700 illustrating portions of a clinician's programmer which can be an embodiment of the CP 628 (FIG. 6). The CP 1700 includes a control circuitry 1702 (e.g., a central processor unit (CPU)) and memory 1704 that stores a stimulation programming package 1706, which can be executed by the control circuitry 1702 to allow the user to program the IPG 626 (FIG. 6), and RC 627 (FIG. 6). The CP 1700 further includes output circuitry 1708 (e.g., via the telemetry circuitry of the RC 627) for downloading stimulation parameters to the IPG 626 and RC 627 and for uploading stimulation parameters already stored in the memory of the RC 627, via the telemetry circuitry of the RC 627.

Execution of the programming package 1706 by the control circuitry 1702 provides a multitude of display screens shown on display 1712 that can be navigated through via use of user input device 1710. These display screens allow the clinician to, among other functions, select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical stimulation energy output by the leads, and select and program the IPG 626 with stimulation parameters in both a surgical setting and a clinical setting.

In various embodiments, execution of the programming package 1706 provides a user interface that conveniently allows a user to program the IPG 626 to produce a user-customized stimulation field, which may include the placement and movement of customized target poles. In various examples, the programming package 1706, when executed by control circuitry 1702, implements a set of engines for facilitating the user interface in which fields or target poles may be defined, mapping the field or target pole definitions to physical electrodes and electrical energy application parameters for establishing the defined fields and target poles, supervising the establishment and variation of the fields and target poles to comply with safety and other defined constraints, and optimizing the energy utilization in the operation of the IPG 626.

In the examples described above, and in various other embodiments, the components described herein are implemented as engines, circuits, components, modules, or other structures, which for the sake of consistency are termed engines, although it will be understood that these terms may be used interchangeably. Engines may be hardware, software, or firmware communicatively coupled to one or more processors in order to carry out the operations described herein. Engines may be hardware engines, and as such, engines may be considered tangible entities capable of performing specified operations and may be configured or arranged in a certain manner. In an example, circuits may be arranged (e.g., internally or with respect to external entities such as other circuits) in a specified manner as an engine. In an example, the whole or part of one or more hardware processors may be configured by firmware or software (e.g., instructions, an application portion, or an application) as an engine that operates to perform specified operations. In an example, the software may reside on a machine-readable medium. In an example, the software, when executed by the underlying hardware of the engine, causes the hardware to perform the specified operations. Accordingly, the term hardware engine is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein.

Considering examples in which engines are temporarily configured, each of the engines need not be instantiated at any one moment in time. For example, where the engines comprise a general-purpose hardware processor core configured using software; the general-purpose hardware processor core may be configured as respective different engines at different times. Software may accordingly configure a hardware processor core, for example, to constitute a particular engine at one instance of time and to constitute a different engine at a different instance of time.

The present inventors have recognized an unmet need to optimally target the neuromodulation to the precise fibers that correspond to the source of pain to be treated, while minimizing stimulation of other fibers in order to reduce or avoid side effects. However, neuromodulation with desirable precision can be challenging. For example, at spinal cord regions near the lumber roots, fiber activation properties may change drastically depending on relative location of a neuromodulation electrode with respect to the neural element of interest. Determining an appropriate stimulation field and electrode configuration for delivering pain therapy at those spinal cord regions, such as via a laterally placed neuromodulation lead, can be technically difficult and time-consuming.

One aspect of the embodiments discussed in this document is directed to optimizing a target neuromodulation field design, and applying a stimulation field to specific neural elements (e.g., dorsal roots) by an IPG such as neuromodulation device 212 (FIG. 2) or IPG 626 (FIG. 6). According to some embodiments, a neuromodulation system such as system 210 (FIG. 2) or the SCS system of FIG. 6, facilitates the creation of a target neuromodulation field by incorporating patient information on dermatomal coverage. An exemplary neuromodulation system includes a processor circuit configured to generate an indication of spatial correspondence between body sites experiencing pain perception and body sites experiencing paresthesia over one or more dermatomes, determine an anodic weight and a cathodic weight for each of the electrode locations using the indication of spatial correspondence, and generate a stimulation field definition using the determined anodic and cathodic weights corresponding to different electrode locations. The stimulation field definition includes parameters such as field size, shape, and intensity, and field scaling and steering parameters. Based on the stimulation field definition, the processor circuit may determine electrode configuration such as fractionalizing current to individual electrodes.

Figure 18:
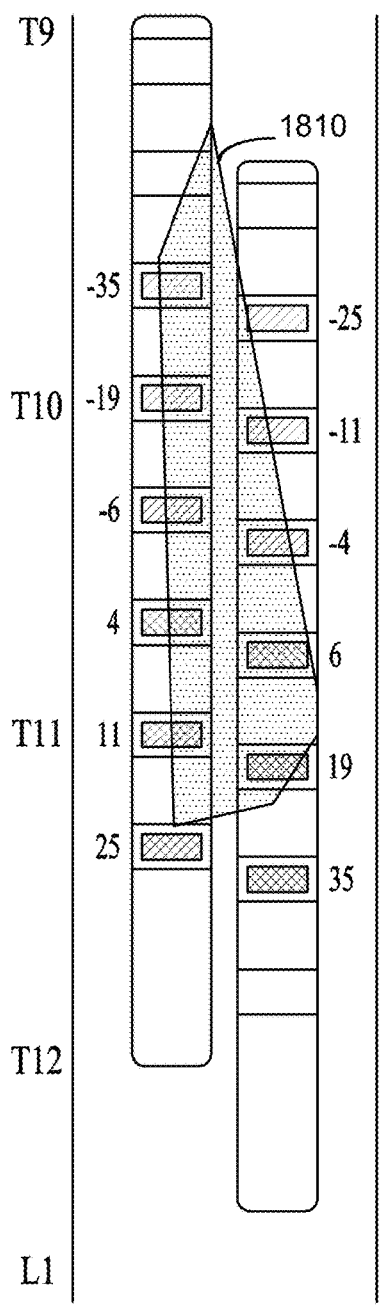
FIGS. 18 and 19 are diagrams illustrating, by way of example and not limitation, anatomical regions on a patient body where pain is felt, or anatomical region on a patient body where neurostimulation effect such as paresthesia is perceived.
Figure 19:
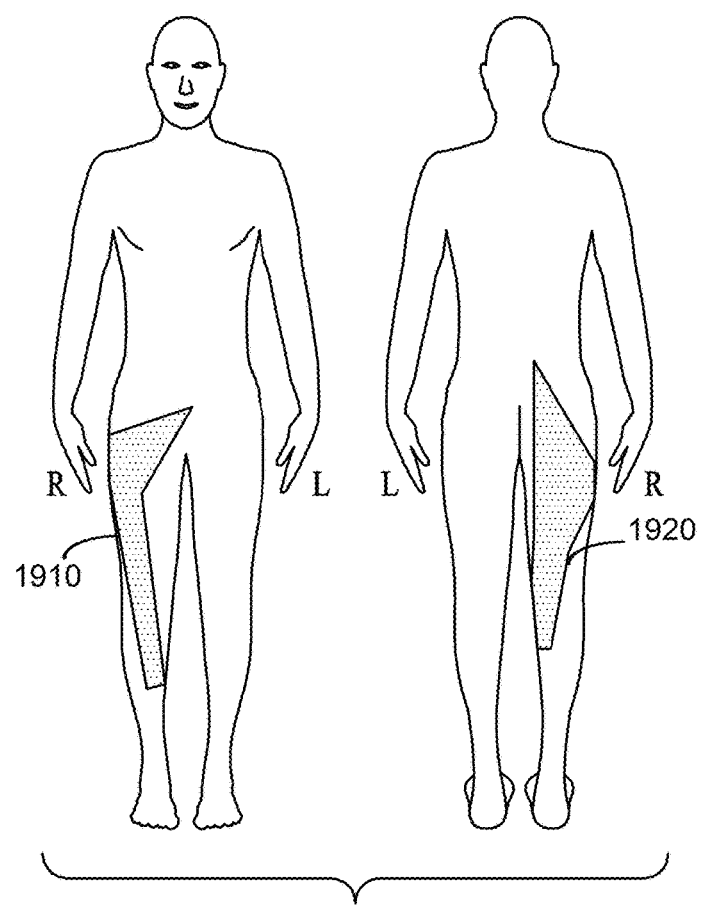

FIGS. 18 and 19 are diagrams illustrating, by way of example and not limitation, anatomical regions on a patient body where pain is felt (pain sites), or anatomical region on a patient body where the effect of neurostimulation delivery, such as paresthesia, is perceived (paresthesia sites). The anatomical sites may be drawn (e.g., free-hand drawing by the patient), derived from a patient pain drawing or paresthesia drawing via a look up table or an algorithm, or using a combination of the methods thereof. FIG. 18 illustrates an example of a drawing 1800 of target sites over a representation of a plurality of electrodes implanted in a patient. The target sites may be pain sites (in which case the drawing 1800 is referred to as a pain drawing), or paresthesia sites (in which case the drawing 1800 is referred to a paresthesia drawing). FIG. 19 illustrates, by way of example and not limitation, drawings representing pain sites or paresthesia sites on an illustrative diagram of a human body including one or both of ventral or dorsal depiction of the body. In the illustrated example, pain sites or the paresthesia sites are marked in a first drawing 1910 on a ventral depiction of the body, and in a second drawing 1920 on a dorsal depiction of the body. The pain drawing and the paresthesia drawing may be respectively generated, and provided to a neuromodulation control system to generate an indication of spatial correspondence between the pain sites and the paresthesia sites. The paresthesia sites may be mapped to specific dermatome compartments on the skin. The mapping may be a point-by-point mapping via a look-up table or a dictionary/key system. The center, length, and width of the target linear field may be determined based on the spatial extent of the spinal cord region corresponding to the patient's reported pain region. A clinician or other specialist, a patient or a combination of persons may work together to highlight region of spinal cord and/or body where they want stimulation to be targeted (i.e. focus stimulation on anatomical correlate and/or reported site of pain). Internal look-up table and/or inverse algorithm with field "primitives" tied to specific regions/region sizes may be used to display and configure electrode settings according to this anatomically-based specification. The neuromodulation control system may determine a stimulation field definition, and calculate electrode fractionalization for a plurality of electrodes, examples of which are discussed below.

Figure 20:
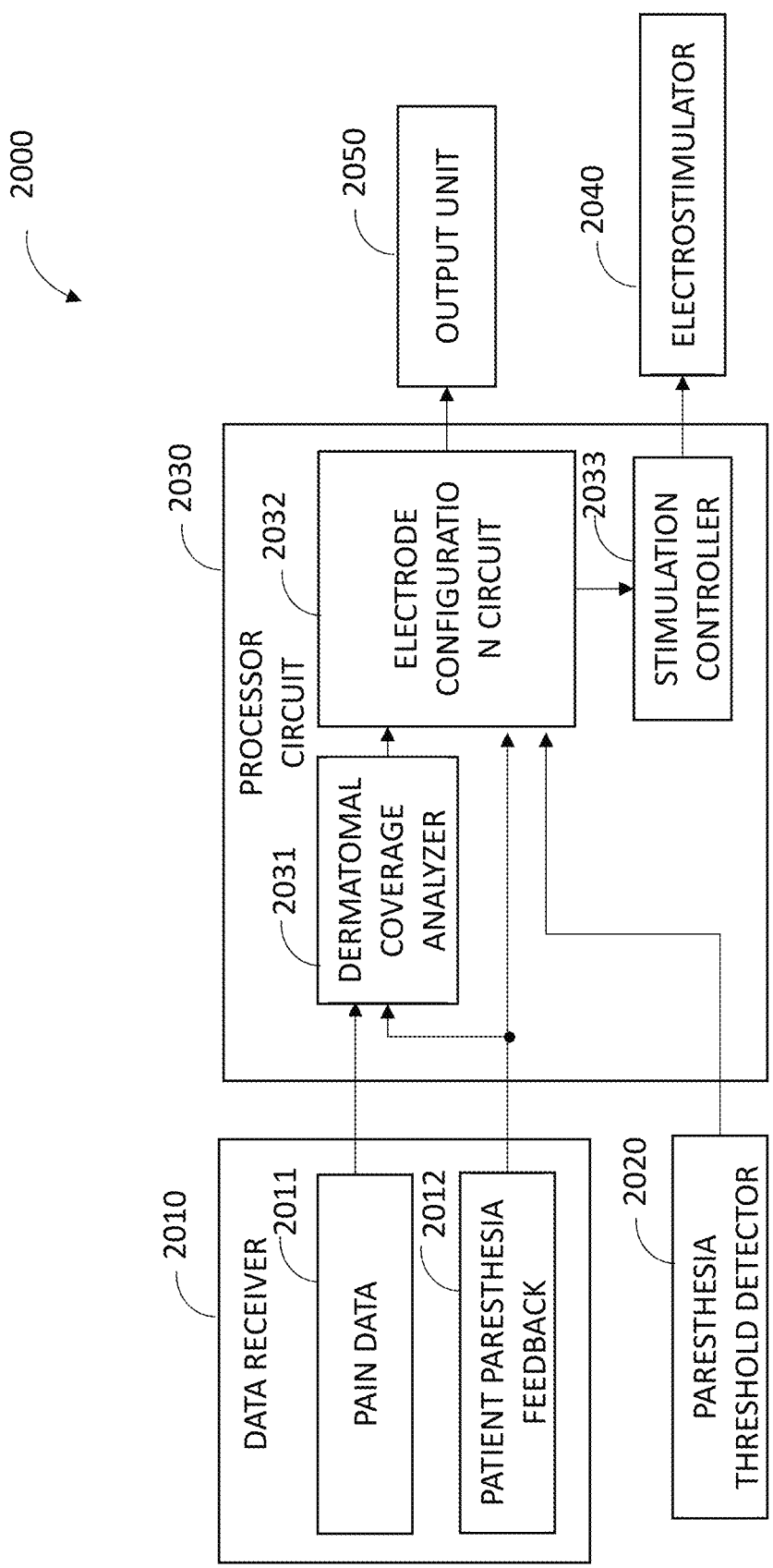
FIG. 20 is a block diagram illustrating, by way of example and not limitation, a neuromodulation system for pain control based on focal dermatomal coverage in a patient.

FIG. 20 is a block diagram illustrating, by way of example and not limitation, a neuromodulation system 2000 configured to provide spinal cord stimulation (SCS) for pain control. The neuromodulation system 2000, which is an embodiment of the neuromodulation system 210, can include one or more of a data receiver 2010, a paresthesia threshold detector 2020, a processor circuit 2030, an electrostimulator 2040, and an output unit 2050. Portions of the neuromodulation system 2000 may be implemented in the implantable system 521 or the external system 522.

The data receiver 2010 may receive, among other things, pain data 2011 and patient paresthesia feedback 2012. The pain data 2011 may include information of anatomical locations of the pain perceived by the patient (pain sites). The pain data 2011 may additionally include one or more of distribution of the pain, intensity of pain at various pain sites, or temporal pattern such as persistence of the pain at various pain sites, among other pain information. The pain data 2011 may be represented by texts, graphs, verbal description, among other means of representation. In an example, the pain data 2011 includes a pain drawing, such as the example illustrated in FIG. 19. The pain drawing may include pain markings, provided by the patient, that identify the locations where pain radiates or expands. The pain markings may additionally include different symbols to distinguish various pain sensations, such as aching, numbness, burning, stabbing, or needle pain. Additionally or alternatively, the pain markings may include different symbols to distinguish various intensities of the pain at each marked pain location. In some examples, the pain data 2011 may include a patient questionnaire or patient pain description. In some examples, the pain data 2011 may include reference data, such as a dermatome map that identifies (e.g., using labels, markers, or annotations) various skin areas corresponding to spinal nerves that innervates said skin areas.

The patient paresthesia feedback 2012 represents patient response to the electrostimulation that induces paresthesia. Paresthesia may be induced using a neurostimulator, such as the electrostimulator 2040, which may be programmed to deliver neuromodulation energy to the target tissue according to a stimulation setting via a set of electrodes at respective electrode locations. Examples of the target tissue may include a portion of a spinal cord, one or more spinal nerves, dorsal roots, or dorsal root ganglia. The stimulation setting may include a location of central point of stimulation (CPS) that represents a focal point of a stimulation field. The stimulation setting may additionally or alternatively include one or more stimulation parameters (also referred to as a neuromodulation parameter set). Examples of the stimulation parameters may include a current amplitude or a voltage amplitude, a pulse width, a pulse shape (waveform), a pulse rate, or a duty cycle, among other parameters.

The CPS location may be adjusted manually or automatically using a trolling process, such as using MICC or multiple independent voltage control, or with a timing channel interleaving technique. The CPS may be trolled up and down (i.e., rostrocaudally) along the lead. This would move the locus of the neuromodulation across different spinal cord locations or different neural structures (e.g., spinal nerves, dorsal roots, or dorsal root ganglia). Trolling may be performed using a monopolar troll (e.g., anodic trolling or cathodic trolling), a bipolar troll, or a multipolar troll algorithm. In an example, trolling may be activated and manipulated manually by a system operator (e.g., a clinician) through a programmer device, such as one of the programming device 213, 413, or 628. Alternatively, trolling may be performed automatically, such as by moving the locus of the neuromodulation in a specific direction and delivering electrostimulation at specific locations within a specified permissible extent (e.g., a lumbar region).

The electrostimulator 2040 can stimulate the target tissue at each of a plurality of manually or automatically set CPS locations to induce paresthesia. At a CPS location, one or more stimulation parameters (e.g., pulse rate, amplitude, stimulation rate, etc.) may be adjusted, and neuromodulation energy may be delivered in accordance with the adjusted stimulation parameters. In an example, different values may be manually programmed by a user, or automatically selected from pre-determined parameter values such as by the stimulation controller 2033. In an example, the stimulation controller 2033 may trigger the electrostimulator 2040 to deliver neuromodulation energy according to a paresthesia induction protocol to scan through a range of pre-determined values of a stimulation parameter (e.g., pulse widths of 100 μs, 300 μs and 500 μs), or a combination of values of two or more stimulation parameters.

The patient paresthesia feedback 2012 may include information of body sites where the effects of neurostimulation, such as paresthesia, is perceived (paresthesia sites). Similar to pain data 2011, the patient paresthesia feedback 2012 may be represented by texts, graphs, verbal description, among other means of representation. In an example, the patient paresthesia feedback 2012 may include a paresthesia drawing of the paresthesia sites, such as the example illustrated in FIG. 19. The paresthesia drawing may be produced by the patient. Alternatively, the paresthesia drawing may be generated using sensor data acquired from, for example, pain sites. Examples of the sensors for sensing patient physiologic response to paresthesia are discussed below, such as with reference to FIG. 21.

The patient paresthesia feedback 2012 may include a patient comfort indicator of the induced paresthesia. The patient comfort indicator may have a categorical value or a numerical value. In an example, the patient comfort indicator may be represented by a preference score representing a degree of patient preference of the induced paresthesia, or a side-effect score representing a degree of side effects of the induced paresthesia (e.g., unwanted reflex or twitch). In an example, the preference score or the side-effect score each has a value in a scale of 0-5. A preference score of "0" indicates a lowest preference and "5" indicates a highest preference. Similarly, a side-effect score of "0" indicates no perceptible side effect and "5" indicates a maximal level of side effects. The patient comfort indicator, such as the preference score of the side-effect score, may be provided by the patient. Additionally or alternatively, the patient comfort indicator may be determined using sensor signals acquired from the patient, such as electromyography (EMG), electrospinogram (ESG), evoked compound action potential (eCAP), among others. For example, preference scores or side-effect scores may be determined based on a comparison of a metric of the sensor signal (e.g., amplitude, frequency, or signal power) to multiple threshold values. As to be discussed in the following, the patient comfort indicator (e.g., the preference score or the side-effect score) may be used to determine or adjust an anodic weight or a cathodic weight at the corresponding electrode location.

The paresthesia threshold detector 2020 is configured to determine for each of the electrode locations a corresponding perception threshold of paresthesia. A perception threshold represents a minimum stimulation energy (e.g., an amplitude threshold of stimulation current) required to elicit a sensation of paresthesia in a patient. The paresthesia perception threshold may be used to determine the field strength of therapeutic sub-perception stimulation for pain relief. In an example, the sub-perception stimulation may be delivered within a range of 30% to 90% of the paresthesia perception threshold. As to be discussed in the following, the paresthesia perception threshold may be used to determine or adjust an anodic weight or a cathodic weight at the corresponding electrode location. According to various embodiments such as the examples to be discussed in the following with reference to FIG. 21, the paresthesia perception threshold may be determined using one or more of patient paresthesia feedback 2012 (e.g., patient comfort indicator), sensor signals, or information about neuroanatomy of the target tissue.

The processor circuit 2030 is configured to determine an optimal stimulation field definition and electrode fractionalization for use in sub-perception pain therapy. The processor circuit 2030 may include circuit sets comprising one or more other circuits or sub-circuits, such as a dermatomal coverage analyzer 2031, an electrode configuration circuit 2032, and a stimulation controller 2033. The circuits or sub-circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

In various examples, portions of the functions of the processor circuit 2030 may be implemented as a part of a microprocessor circuit. The microprocessor circuit can be a dedicated processor such as a digital signal processor, application specific integrated circuit (ASIC), microprocessor, or other type of processor for processing information including physical activity information. Alternatively, the microprocessor circuit can be a general purpose processor that can receive and execute a set of instructions of performing the functions, methods, or techniques described herein.

The dermatomal coverage analyzer 2031 is configured to generate an indication of spatial correspondence between the pain sites and the paresthesia sites over one or more dermatomes. In an example, said spatial correspondence may be represented by an overlapping area between a pain drawing and a paresthesia drawing (also referred to as pain-paresthesia overlapping area, or $S_{PPO}$, in this document). The $S_{PPO}$ may be determined across one or more dermatomes. A dermatome is an area of skin that is supplied by sensory neurons that arise from a spinal nerve ganglion. Originating from the spinal cord there are eight cervical nerves (C1 through C8), twelve thoracic nerves (T1 through T12), five lumbar nerves (L1 through L5), and five sacral nerves (S1 through S5). Each of these nerves relays sensations, including pain, from a particular region of skin to the brain. Successful pain management and the avoidance of stimulation in unafflicted regions require the applied electric field to be properly positioned longitudinally along the dorsal column. Each of the spinal nerves (including cervical nerves C2-C8, thoracic nerves T1-T12, lumbar nerves L1-L5, and sacral nerves S1-S5) can be mapped to a respective dermatome.

In an example, the pain sites and the paresthesia sites may each be mapped dermatomes. Accordingly, the overlapping region between pain and paresthesia sites may also be mapped to one or more dermatomes. In an example, the dermatomal coverage analyzer 2031 may pixelate the pain drawing into pixels on the pain sites. The dermatomal coverage analyzer 2031 may similarly pixelate the paresthesia drawing into pixels on the paresthesia sites. The pixels can be represented by respective pixel coordinate corresponding to anatomical point locations of the subject. In various examples, each pixel can be associated with respective pain descriptors that indicate one or more of presence, intensity, or temporal pattern of pain at the corresponding pixel. The pain-paresthesia overlapping area may be measured using a count of pixels within the pain-paresthesia overlapping area. The pain-paresthesia overlapping area may be determined for each of one or more dermatomes. In another example, the dermatomal coverage analyzer 2031 may determine the dermatomal coverage using numeric entry of pain or paresthesia perception from a gridded dermatome map, or by extracting information from a patient questionnaire that includes a selectable list of anatomical regions (corresponding to dermatomal compartments) and locations experiencing pain or paresthesia, such as lower back, hip, inner thigh, outer thigh, knee, foot, ankle, calf, etc., optionally with additional site specificity (e.g., left/right, front/back).

The electrode configuration circuit 2032 may determine an optimal stimulation field definition and electrode fractionalization using one or more of the pain-paresthesia spatial correspondence indication (e.g., pain-paresthesia overlapping area over a number of dermatomes) generated by the dermatomal coverage analyzer 2031, the patient paresthesia feedback 2012, or the paresthesia perception threshold generated by the paresthesia threshold detector 2020. The stimulation field definition includes parameters such as field size, shape, and intensity, and field scaling and steering parameters. The optimal stimulation field definition may be determined using anodic weight and cathodic weight for each electrode location. In an example, the anodic and cathodic weights may be determined using a linear or nonlinear combination of some or all of the pain-paresthesia overlapping area, the patient paresthesia feedback, and the paresthesia perception threshold. Based on the optimal stimulation field definition, the electrode configuration circuit 2032 may individually regulate neuromodulation energy (e.g., electrical current) to individual ones of a set of electrodes, a process also referred to as energy or current fractionalization among electrodes, or fractionalized electrode configuration. Electrodes thus configured may then be used to establish a stimulation field to modulate target tissue for pain relief. In an example, the stimulation field definition may be first determined using information of pain-paresthesia correspondence, and one or more of the patient paresthesia feedback or the paresthesia threshold may be used to adjust the stimulation field definition. Examples of the electrode configuration using any or all of the pain-paresthesia overlapping area, the patient paresthesia feedback, and the paresthesia perception threshold are discussed below, such as with reference to FIG. 23.

Information of electrode configuration, such as the optimal stimulation field definition and electrode fractionalization, may be presented to a user or a process. In an example, the output unit 2050 may include a user interface, such as one of the GUI 214 or 414 of the programming device 213, 413, or 628. The user interface may be configured to display the information of electrode configuration, among other information such as the pain-paresthesia overlapping area over a number of dermatomes, the patient paresthesia feedback, and the paresthesia perception threshold.

The stimulation controller 2033 may generate a control signal for adjusting the stimulation setting, such as by trolling the CPS location or tuning one or more stimulation parameters (e.g., pulse width, amplitude, duty cycle, stimulation rate, etc.). The control signal may trigger the electrostimulator 2040 to deliver a first type neuromodulation energy at the target tissue to induce paresthesia according to the adjusted stimulation setting. Additionally, the stimulation controller 2033 may be configured to generate a control signal for triggering the electrostimulator 2040 to deliver a second type of neuromodulation energy, such as sub-perception stimulation energy, at the target tissue to relieve pain via the set of electrodes in accordance with the fractionalized electrode configuration as determined by the electrode configuration circuit 2032. The sub-perception stimulation energy may be delivered using monophasic stimulation pulses applied to each electrode, which can be used as either an anode or cathode in accordance with the fractionalization configuration. Alternatively, the sub-perception stimulation energy may be delivered using biphasic stimulation pulses. Each biphasic pulse has a first phase of a first polarity followed by a second phase of a second polarity opposite of the first polarity. The first and second phases can be symmetric (e.g., the same magnitude or duration). Alternatively, the first and second phases can be asymmetric. Because of opposite polarities of the two phases in a stimulation pulse, the electrode polarity (i.e., designation of an electrode as an anode or as a cathode) as defined by the electrode configuration circuit 2032 would flip when the stimulation current changes from the first phase to the second phase. In an example, the electrode configuration circuit 2032 may modify the cathode and anode designation based on the first phase of the biphasic pulse. For example, if the first phase is positive, then no modification is made to the anode and cathode that have been determined. If the first phase is negative, then the anode and cathode designation are swapped. In an example, asymmetric biphasic stimulation may be delivered to both a preferred stimulation site and a site where stimulation is to be avoid. At the preferred stimulation site, the biphasic stimulation can include a first anodic phase with a longer duration and smaller magnitude, followed by a second cathodic phase with a shorter duration and larger magnitude. At the region to avoid, biphasic stimulation can include a first cathodic phase with a longer duration and smaller amplitude (sub-threshold for its pulse width), followed by a second anodic phase with a shorter duration and higher amplitude for charge balance.

The electrostimulator 2040 can be an implantable module, such as incorporated within the implantable system 521. Alternatively, the electrostimulator 2040 can be an external stimulation device, such as incorporated with the external system 522. In an example, the first and second types of neuromodulation energy may be delivered respectively through separate first and second channels of the electrostimulator 2040. In various examples, the first and second types of neuromodulation energy may be generated and delivered respectively by different electrostimulator. For example, an external electrostimulator may be used to generate the first type of neuromodulation energy for paresthesia induction, and an implantable electrostimulator may be used to generate the second type of neuromodulation energy as a mode of pain therapy.

Figure 21:
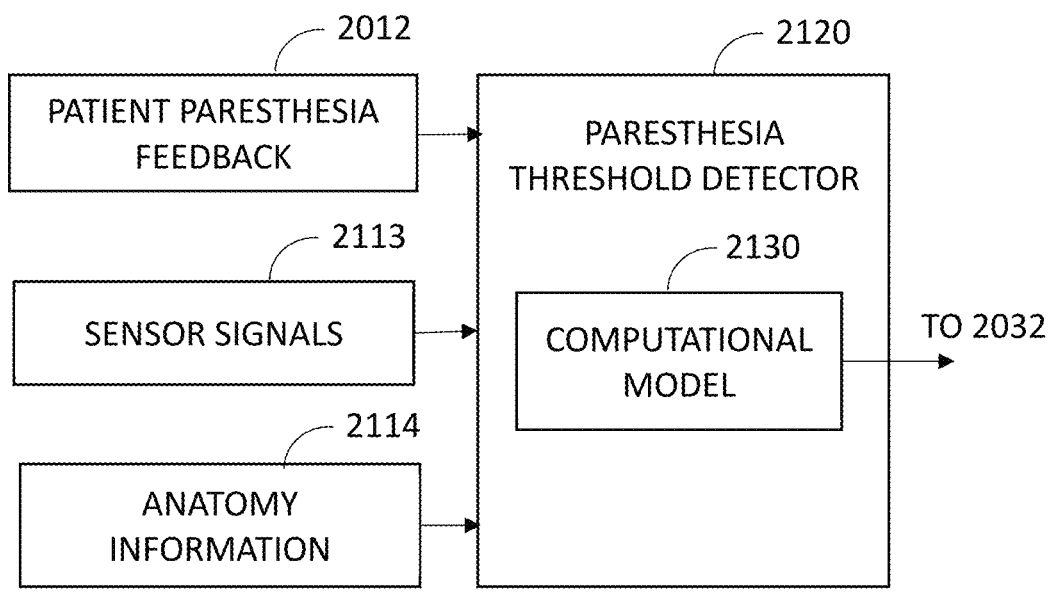
FIG. 21 is a block diagram illustrating, by way of example and not limitation, a paresthesia threshold detector to determine a perception threshold of paresthesia.

FIG. 21 is a block diagram illustrating, by way of example and not limitation, a paresthesia threshold detector 2120 configured to determine for each of a plurality of the electrode locations a corresponding paresthesia perception threshold. The paresthesia threshold detector 2120, which is an embodiment of the paresthesia threshold detector 2020, may determine a paresthesia perception threshold using one or more of a patient paresthesia feedback 2012, sensor signals 2113, or anatomy information 2114. The patient paresthesia feedback 2012 may include a patient comfort indicator as discussed above. The sensor signals 2113 represents patient physiological response to the induction of paresthesia that can be sensed by one or more sensors. In an example, paresthesia sites are first identified, and one or more sensor are then positioned at the identified paresthesia sites. In another example, one or more sensors may be positioned at one or more pain sites prior to paresthesia induction. This allows the sensors to pick up patient physiological signals from the pain-paresthesia overlapping areas. In some examples, one or more sensors are implantable sensors, such as associated with a neuromodulation lead or a separate implantable device, placed over regions of dorsal column or dorsal roots.

By way of example and not limitation, the sensors may include one or more electromyography (EMG) sensors. The EMG sensors may be patches configured for external placement over the skin area experiencing paresthesia. In an example, the EMG sensors may be bilaterally placed (left and right), and/or placed on both the front and back of the patient. The EMG sensors may be implantable sensors such as associated with the implantable lead. In some examples, the EMG signals acquired by an EMG sensor may be used to characterize side effects of paresthesia, such as motor twitching. Such sensor feedback on paresthesia may be part of the patient paresthesia feedback 2012 for determining paresthesia threshold. The EMG signals may be recorded and processed, such as via the paresthesia threshold detector 2120, to derive one or more EMG variables such as amplitude information, timing information (e.g., onset timing with respect to stimulation pulse), frequency or spectral content information, among others. These values may be absolute values, or relative values such as between different EMG electrodes, between different dermatomes, or between left and right sides or between front and back of the patient.

In some examples, the sensors may include electrospinogram (ESG) sensor configured to sense electrical activity (e.g., electrical field potential) of the spinal cord or the affiliated neural structures such as dorsal roots or spinal nerves. In another example, the sensors may include electrically evoked compound action potential (eCAP) sensor configured to sense a change in eCAP produced by electrostimulation. The ESG or the eCAP sensors may be placed on the paresthesia sites, or implanted such as associated with a neuromodulation lead or as a separately implanted device. In another example, the sensors may include one or more impedance sensors configured to sense tissue impedance at the paresthesia sites. The change in tissue impedance is correlated with paresthesia and muscle twitches produced by paresthesia-inducing electrostimulation. The sensor signals 2113 may be monitored during an implant of a neuromodulation device or in an outpatient setting.

The anatomy information 2114 may include neuroanatomy of at least a portion of the patient spinal cord or the associated neural structures, such as dorsal roots, ventral roots, dorsal root ganglia, or lumbar spinal nerves. By way of example and not limitation, the neuroanatomy information may include size, shape, or other geometric or morphological metrics of the spinal cord or the associated neural structures, a trajectory or an entry pattern of one or more dorsal roots, spatial proximity of the electrode with respect to one or more dorsal roots, or anatomical references (e.g., vertebral level or pedicles).

The paresthesia threshold detector 2120 may use any of the patient paresthesia feedback 2012, sensor signal 2113, or the anatomy information 2114 to determine a paresthesia perception threshold. In an example, the perception threshold may be determined using a computational model 2130. The computational model 2130 can be a field element model of the spinal cord that characterizes the neuroanatomical and physical properties of a portion of the spinal cord, the stimulation filed, and tissue-electrode interactions. The computational model 2130 may be in a form of a parametric model, a statistical model, a shape-based model, a volumetric model. The computational model 2130 can be a numerical model (e.g., a look-up table, a database, or other data structure) or an analytical model. In an example, the computational model 2130 is a finite element method (FEM) model, or an approximation of a FEM model, of target tissue such as a portion of spinal cord or neural structures thereof (e.g., dorsal roots or spinal nerves). The computational model 2130 may be created off-line, adjusted and optimized for individual patient such as based on patient-specific subjective input and objective neurophysiological and neuroanatomical measurements obtained from the patient paresthesia feedback 2012, sensor signal 2113, or the anatomy information 2114. The individualized computational model 2130 may be uploaded to a neuromodulation device to characterize individualized perception threshold, and identify target tissue to stimulate with improved precision. According to various embodiments, one or more of dorsal column, dorsal horn, dorsal roots, or dorsal root ganglia may be targeted. The modulation field of the targeted region may be designed to enhance the neural activity in the targeted region or to inhibit or block the neural activity in the targeted region. The perception threshold detected by the paresthesia threshold detector 2120 may be provided to the electrode configuration circuit 2032 to determine anodic and cathodic weights for each electrode location and determine the fractionalized electrode configuration, examples of which are to be discussed in the following with reference to FIG. 23.

Figure 22A:
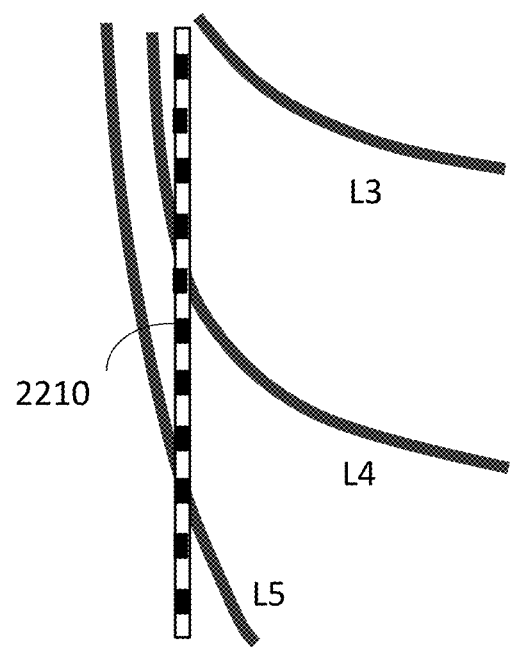
FIGS. 22A-22C are diagrams illustrating, by way of example and not limitation, a computational model of spinal cord and associated neural structures, and activation thresholds at different spinal locations.
Figure 22B:
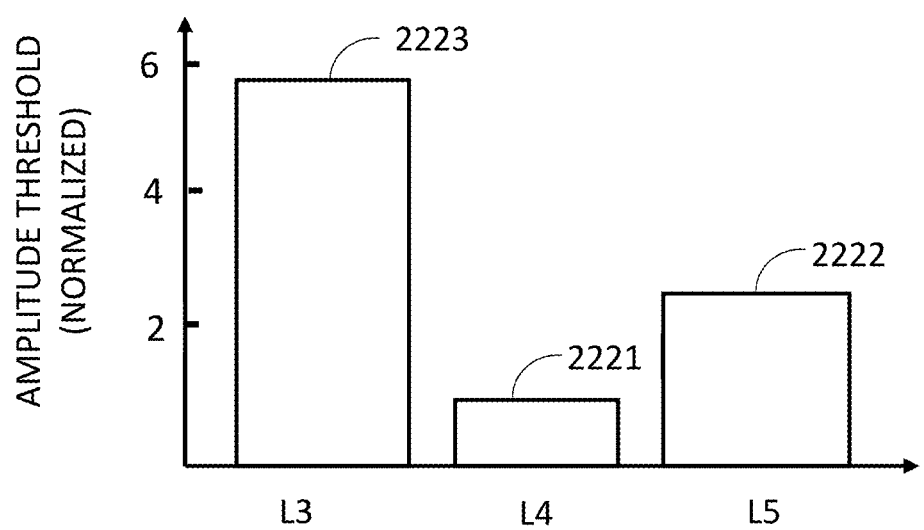
Figure 22C:
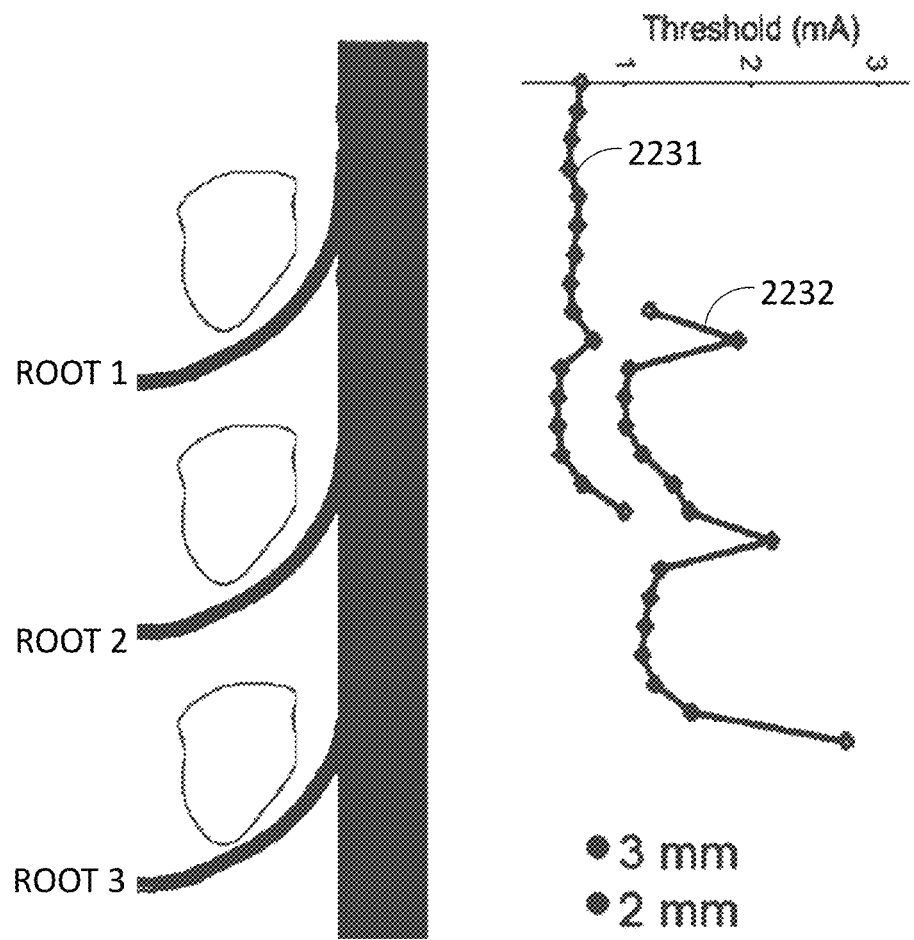

FIGS. 22A-22C are diagrams illustrating, by way of example and not limitation, a computational model of spinal cord and associated neural structures, and activation thresholds at different spinal locations. FIG. 22A illustrates a portion of the lumbar spinal cord and dorsal roots corresponding to lumbar nerves L3, L4, and L5, and a representation of a laterally placed neuromodulation lead representation 2210 disposed at the low thoracic, high lumbar region. In conventional modulation field design for spinal cord stimulation, it is generally assumed that the neuromodulation lead is in parallel to the spinal column, and that the neuromodulation lead makes a substantially uniform entry angle with respect to a number of dorsal column axons of interest. However, dorsal root trajectory changes depending on the vertebral level of the spine. For example, the dorsal roots at vertebral levels T7-T10 are substantially orthogonal to the spinal column at the point of entry. The dorsal roots at this thoracic region generally have a higher threshold than the columns. However, at lumbar vertebral levels such as L3-L5 as shown in FIG. 22A (see also FIGS. 9A-9E), the dorsal roots therein are generally not orthogonal to the spinal column at the point of entry. For lead placements in the lumbar area, the leads are at the level of the cauda equina, where there is virtually no spinal cord, and the dorsal roots form an acute angle (approximately 27-40 degrees) with respect to the rostrocaudal axis of the spinal cord (as opposed to substantially a right angle at the thoracic levels T7-T10). Accordingly, the general assumption of higher dorsal root threshold at the thoracic levels T7-T10 region may not hold for dorsal roots are the lumbar area. As illustrated in FIG. 22A, the lead comes with different angles and spatial proximity to the lumbar roots L3, L4, L5. Differences in dorsal root entry pattern and trajectory, axon geometry, and relative proximity of the stimulation electrodes to the dorsal roots, among other things, may result in different activation patterns in the lumbar roots.

The activation of a dorsal root (and thus the associated spinal nerve) may be characterized by respective action potential threshold. FIG. 22B illustrates relative action potential thresholds corresponding to respective dorsal roots L3, L4, and L5. The action potential threshold represents minimum stimulation energy (e.g., current amplitude) required to elicit action potential and to produce paresthesia perception at respective dermatomes innervated by the corresponding lumbar nerves. By way of example and not limitation, the action potential may be sensed using an ESG sensor. The elicited physiological response from the electrical stimulation, for example the paresthesia perception threshold, is correlated in part to the action potential threshold. The action potential threshold is correlated in part to spatial proximity and entry angle between the lead representation and the dorsal roots. When stimulation is provided nearer to a particular dorsal root where neural fiber density is higher, a larger number of neural fibers are recruited and fire, resulting in a greater response (e.g., a higher magnitude of ESG). This corresponds to a lower action potential threshold at the particular dorsal root. In the example shown in FIGS. 22A-22B, action potential thresholds at L3, L4, and L5 differ substantially from one another. For example, L4 has the lowest threshold 2221, at least due to its spatial proximity to the lead representation 2210, and a trajectory almost perpendicular to the lead representation 2210. L5 is also proximal to the lead representation 2210, but comes with a smaller entry angle relative to the lead representation 2210. Accordingly, L5 has a higher threshold 2222. Compared to L4 and L5, L3 is more distant away from the lead representation 2210, thereby having the highest threshold 2223.

FIG. 22C illustrates a portion of a computational model that includes representations of a portion of the spinal cord and dorsal roots from the spinal cord (e.g., Root 1, Root2, and Root 3 as shown). The computational model is an example of the computational model 2130 in FIG. 21. The neuromodulation lead representation 2210 is laterally placed near the spinal cord. FIG. 22C illustrates two lead placement locations, site A and site B. Site A is relatively closer to the Roots 1-3, and site B is relatively farther away from the Roots 1-3. The computational model includes geometric component that describes the dorsal root entry pattern and trajectory, and spatial morphology with respect to the spinal column. The computational model also includes biophysical components that characterize respectively biophysical properties of each of the Roots 1-3. In the illustrated example, the neuromodulation lead representation 2210 has 16 electrodes. For each lead placement (e.g., site A and site B), activation thresholds may be determined respectively from the 16 contact locations. In FIG. 22C, graph 2231 represents activation thresholds (in milliamp, or mA) of 16 electrode contacts obtained during electrostimulation when the lead representation 2210 is placed at site A, and graph 2232 represents activation thresholds of 16 electrode contacts obtained during electrostimulation when the lead representation 2210 is placed at site B. In the illustrated example, the activation thresholds 2231 are consistently lower for all electrodes than the thresholds 2232. For each lead site (site A or site B), the relative spatial proximity of an electrode with respect to a dorsal root may vary. As a result, the activation thresholds vary from one electrode contact to another.

According to various embodiments discussed in this document, the difference in activation threshold at different electrode locations relative to neural targets (e.g., dorsal roots as illustrated in FIGS. 22A-22C) are used to guide neuromodulation field design. The activation threshold may be correlated with paresthesia perception threshold at different dermatomes. In various embodiments, the present subject matter incorporates patient feedback on the induced paresthesia into the process of neuromodulation field design, adjusts stimulation field such as by changing current fractionalization to account for patient paresthesia perception, thereby improving the efficacy of the neuromodulation for pain therapy as well as the device functionality such as energy utilization.

Figure 23:
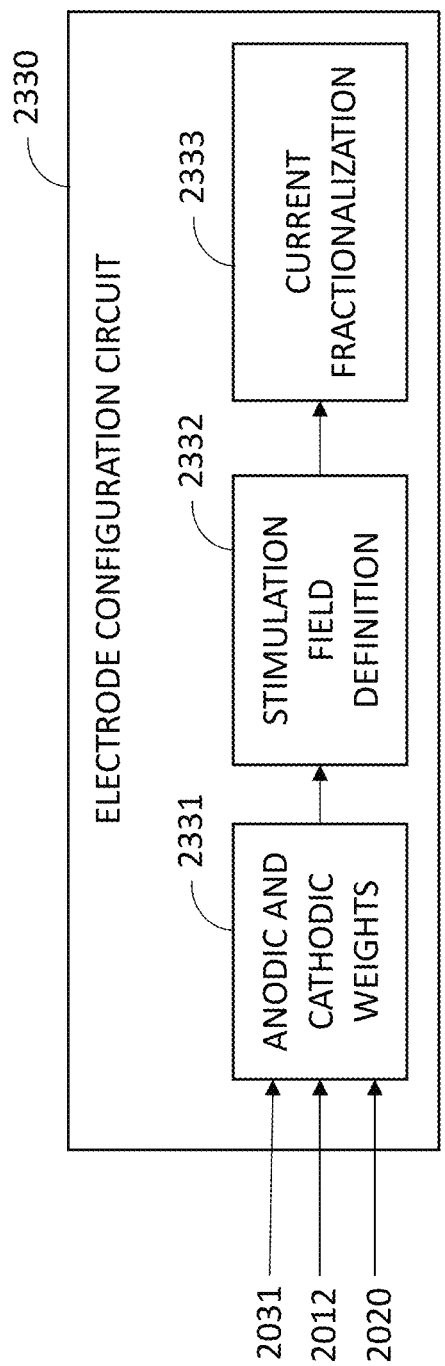
FIG. 23 is a block diagram of an electrode configuration circuit.

FIG. 23 is a block diagram of an electrode configuration circuit 2330, which is an embodiment of the electrode configuration circuit 2032 of FIG. 20. The electrode configuration circuit 2330 can be configured to generate anodic and cathodic weights 2331 for each of a plurality of electrode locations and the paresthesia perception threshold from the paresthesia threshold detector 2020. The anodic and cathodic weights may each be determined using a linear or nonlinear combination of some or all of the pain-paresthesia overlapping area, the patient paresthesia feedback, and the paresthesia perception threshold. In an example, the paresthesia feedback 2012 includes patient comfort level regarding paresthesia, such as a preference score or a side-effect score. The anodic and cathodic weight may each be determined using the patient comfort level and the pain-paresthesia overlapping area. By way of example and not limitation, cathodic weight ($W^+$) may be proportional to a product of the preference score and the pain-paresthesia overlapping area ($S_{PPO}$), and the anodic weight ($W^-$) may be proportional to a product of the side-effect score and an area of the paresthesia drawing ($S_{Pares}$) excluding the overlapping area, such as given in the following Equations (1) and (2):

$$W^+ = \text{Preference score} * S_{PPO} \qquad (1)$$

$$W^- = \text{Side-effect score} * (S_{Pares} - S_{PPO}) \qquad (2)$$

In another example, the anodic and cathodic weights may be determined using a machine learning model. Examples of the ML model may include a regression model, a decision tree, a Naïve Bayes model, a support vector machine model, a K-nearest neighbor model, a random forest model, a neural network model, a voting model, a fuzzy logic model, among others. By incorporating patient feedback on the induced paresthesia (e.g., the preference score or the side-effect score) into the dermatomal coverage of pain (e.g., pain-paresthesia overlapping area), variation in neuroanatomy including locations of neuromodulation electrode relative to the neural structures of interest can be effectively compensated for, and the precision of target stimulation field can be improved. As a result, neuromodulation therapy can be delivered to precise fibers that correspond to the source of pain to be treated, while stimulation of other fibers and side effects can be minimized or avoided.

The anodic and cathodic weights may be used to determine stimulation field definition 2332. The stimulation field definition includes size, shape, and field intensity, as well as scaling and steering of the field. In an example, anodes and cathodes may be set on a lead, such as by determining a net cathode effect or a net anode effect for each electrode, such as according to Equation (3) below:

$$\text{Net Anode/Cathode effect} = (W^+ - W^-) * m \quad (3)$$

As each electrode has an anodic weight $W^+$ and a cathodic weight $W^-$, the electrode has a net anode effect if $W^+ > W^-$, or a net cathode effect if $W^+ < W^-$. In Equation (3), "m" represents a normalization factor that controls a relative strength (proportion) of the anode effect or cathode effect distributed to that electrode. The normalization factors (m's) of all the electrodes with a net anode effect (i.e., satisfying $W^+ > W^-$) add up to 100%. The normalization factors (m's) of all the electrodes with a net electrode effect (i.e., satisfying $W^+ < W^-$) add up to −100%. In another example, the normalization factor may instead or additionally refer to maximum of the anodic or cathodic current. The anode or cathode, respectively, sum up to 100%, while the excess charge from the other polarity will be delivered through a case electrode (e.g., housing of an implantable neuromodulator device such as the neuromodulation devices 212, 312 or 512, or the IPG 626).

The stimulation field definition may be used to generate current fractionalization 2333 to achieve an objective function. An objective function refers to a function with desirable characteristics for modulating the targeted tissue. The objective function may also be referred to as an objective target function. An objective function for a broad and uniform modulation field is identified for a given volume of tissue. Examples of an objective function includes a constant E (electric field), a constant |E| (electric field magnitude), and a constant voltage. Information such as lead and electrode configuration, electrode tissue coupling, electrode contact status, and a threshold such as a current threshold, may be used as input to an electrode energy fractionalizer, which is configured to individually regulate electrical current to individual ones of the set of electrodes based on the stimulation field definition. A function can be performed that is dependent on the objective function, the electrode positions, and the electrode tissue coupling. The result of the function is the fractionalization of modulation energy (e.g. current) for each electrode to achieve the objective function. The fractionalization of modulation energy may be expressed, for each electrode, as a polarity and percentage of the total cathodic energy (add up to 100%) or percentage of total anodic energy (add up to −100%) delivered to the plurality of electrodes on the lead at a given time. Furthermore, an amplitude boost or scaling factor may be applied to the fractionalization values. In some examples, a selected field model may be used to estimate the field induced by unit current from the contact. The field is calibrated using the threshold. Constituent forces are formed based on the selected contacts. A transfer matrix (A) may be constructed, which mathematically describe the electrical behavior of the model. A specified target stimulation field may be provided to the model. The target stimulation field ($\varphi$) can be represented by a central point of stimulation (CPS). The transfer matrix (A) can be used to compute the minimal mean square solution using contributions from the constituent sources and the specified target field. The solution can be used to compute the current fractionalization on each contact.

Figure 24:
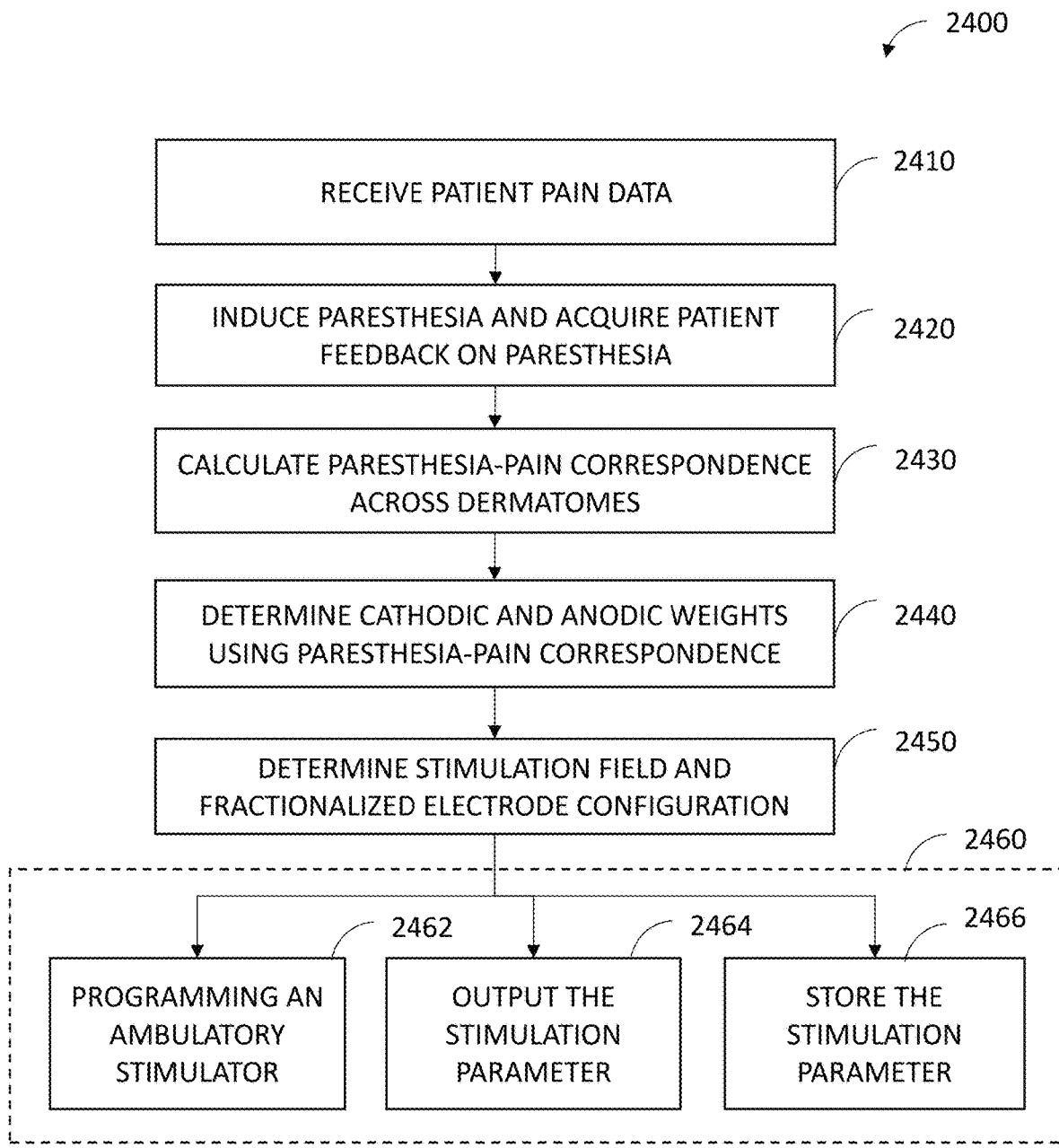
FIG. 24 is a flow chart illustrating, by way of example and not limitation, a method for controlling delivery of electrostimulation to neural targets based on focal dermatomal coverage.

FIG. 24 is a flow chart illustrating, by way of example and not limitation, a method 2400 for controlling delivery of electrostimulation to neural targets based on focal dermatomal coverage, such as a spinal cord, via a medical system such as one of the neuromodulation systems 210 or 2000. Portions of the method 2400 may be implemented in an external device, such as a device in the external system 522, or one of the programming devices 213 or 413, the CP 628, or the RC 627. By executing the method 2400, the programming device or the external device may program a neuromodulation device (e.g., one of the neuromodulation devices 212, 312 or 512, or the IPG 626, or the electrostimulator 2040) to deliver spinal cord stimulation. Although spinal cord stimulation is discussed herein, the method 2400 may be modified to provide stimulation of other neural targets, such as one or more of spinal nerves, dorsal roots, or dorsal root ganglia, among others.

The method 2400 commences at 2410, where patient pain data can be received, such as from a user via the data receiver 2010. The pain data may include information of body sites of pain perception, and optionally pain characteristics of such perception such as distribution, intensity, or temporal pattern of pain. In an example, the pain data includes a pain drawing, such as the example illustrated in FIG. 19. The pain drawing may include pain markings, provided by the patient, that identify the locations where pain radiates or expands. The pain data may include reference data, such as a dermatome map that identifies various skin areas corresponding to spinal nerves that innervates said skin areas.

At 2420, paresthesia may be induced in the patient, and patient feedback to paresthesia may be acquired. Paresthesia may be induced via an implantable or an external neuromodulation device such as the electrostimulator 2040. The induction of paresthesia may include trolling a central point of stimulation (CPS) up and down (i.e., rostrocaudally) along a neuromodulation lead that includes a set of electrodes at respective electrode locations, thereby moving the locus of the neuromodulation across different spinal cord locations or different neural structures. One of a monopolar, a bipolar, or a multipolar troll algorithm may be used. At each of a plurality of CPS locations, neuromodulation energy may be delivered to induce paresthesia. One or more stimulation parameters (e.g., pulse rate, amplitude, stimulation rate, etc.) may be adjusted, and neuromodulation energy may be delivered in accordance with the adjusted stimulation parameters.

The patient paresthesia feedback may include information of body sites experiencing paresthesia perception by the patient. In an example, the patient paresthesia feedback may include a paresthesia drawing, such as the example illustrated in FIG. 19. The paresthesia drawing may be manually produced by the patient, or alternatively be generated using sensor data acquired from pain sites. In some examples, the patient paresthesia feedback may include a patient comfort indicator, such as a preference score representing a degree of patient preference of the induced paresthesia or a side-effect score representing a degree of side effects of the induced paresthesia (e.g., unwanted reflex or twitch). In an example, the preference score and the side-effect score may each take a numerical value in a scale of 0-5, respectively indicting a degree of preference or a degree of side effect of paresthesia induction.

At 2430, a paresthesia-pain correspondence may be determined across a number of dermatomes, such as by using the dermatomal coverage analyzer 2031 of the neuromodulation system 2000. The paresthesia-pain correspondence may be represented by an overlapping area ($S_{PPO}$) between a pain drawing and a paresthesia drawing. In an example, the pain drawing received at 2410 and the paresthesia drawing as determined at 2420 may each be pixelated into pixels of images. The pixelated pain drawing and the pixelated paresthesia drawing may each be mapped a number of dermatomes. The overlapping region between pain and paresthesia sites may also mapped to one or more dermatomes. The pain-paresthesia overlapping area, $S_{PPO}$, may be measured using a count of pixels within the pain-paresthesia overlapping area. In an example, the pain-paresthesia overlapping area may be determined for each of one or more dermatomes.

At 2440, anodic and cathodic weights may be determined for each of a plurality of electrode locations. In an example, the anodic and cathodic weights may be determined using the paresthesia-pain correspondence determined at 2430 and the patient feedback (e.g., the preference score and the side-effect score) generated at 2420, such as according to the Equations (1) and (2).

In some examples, the anodic and cathodic weights may be determined at 2440 further using information of paresthesia perception threshold, such as determined using one of the paresthesia threshold detectors 2020 or 2120. The perception threshold represents a minimum stimulation energy (e.g., an amplitude threshold of stimulation current) required to elicit a sensation of paresthesia in a patient. An example of determining the perception threshold is discussed above with reference to FIG. 21, where the paresthesia perception threshold may be determined using one or more of the patient paresthesia feedback, sensor signals, or anatomy information. Examples of the sensor signals may include EMG signals, eCAP signals, ESG signals, or tissue impedance signals. Examples of anatomy information may include size, shape, or other geometric or morphological metrics of the spinal cord or the associated neural structures (e.g., dorsal roots, ventral roots, dorsal root ganglia, or spinal nerves), a trajectory or an entry pattern of one or more dorsal roots, spatial proximity of the electrode with respect to one or more dorsal roots, or anatomical references, among others.

In an example, the anodic and cathodic weights may be determined using a linear or nonlinear combination of some or all of the pain-paresthesia overlapping area, the patient paresthesia feedback, and the paresthesia perception threshold. In an example, the paresthesia threshold may be determined using any a computational model, such as a FEM model. FIGS. 22A-22C illustrates different activation thresholds at various electrode locations relative to neural targets. These examples demonstrate that complex anatomical structures of the neural target, such as lumber dorsal roots of a spinal cord, may pose a challenge to design neuromodulation field that activate the precise fibers that correspond to the source of pain to be treated, while minimize stimulation of other fibers in order to reduce or avoid side effects. By incorporating patient feedback on the induced paresthesia into the process of neuromodulation field design, the systems and methods discussed herein allow proper adjustment of stimulation such as by changing current fractionalization to account for patient paresthesia perception. This may not only improve the neuromodulation precision and thus better therapeutic outcome, but may also save a system operator's time and ease the burden of programming a neuromodulation system.

At 2450, stimulation field and fractionalized electrode configuration may be determined using the cathodic and anodic weights for each of a plurality of electrodes, such as using the electrode configuration circuit 2330. The anodic and cathodic weights obtained at 2440 may be used to determine a target stimulation field definition, which defines size, shape, and field intensity, as well as scaling and steering of the field. In an example, anodes and cathodes may be set on a lead such as according to Equation (3). The target stimulation field definition may be mapped to electrode polarities and current fractionalization for the electrodes on the stimulation lead. In an example, the mapping involves application of a transfer matrix to the target stimulation field definition. The transfer matrix may be used to compute relative strengths of a plurality of constituent current sources needed to match the target stimulation field definition at the spatial observation points when a specified optimization criterion is satisfied. In another example, the mapping involves a regression fitting of the target stimulation field definition, such as by using a linear or nonlinear regression model. In an example, the mapping may involve a least-square fitting of the target electrical field.

The fractionalized electrode configuration, including the electrode polarities and current fractionalization, among other parameters such as boost or scaling factors, may be output to a user or a process at 2460. In an example, at 2462, the fractionalized electrode configuration may be programmed to a neuromodulation device, such as via a programming device or the stimulation controller 2033. The programming of the neuromodulation device may be carried out automatically or triggered by a user command or a specific event. A programming control signal may be communicated to the neuromodulation device via a communication link such as the wireless communication link. In response to the control signal, the neuromodulation device may deliver neuromodulation energy, such as sub-perception stimulation energy, at the target tissue (e.g., spinal cord or associated neural structures) in accordance with the fractionalized electrode configuration to relieve pain. In another example, at 2464, the fractionalized electrode configuration, among other information such as optimal stimulation field definition or stimulation parameter set, may be presented to a system user (e.g., a clinician), such as displayed on a user interface of the output unit 2050, or the GUI 214 or 414 of the programming device 213, 413, or 628. The user may adjust the stimulation parameter through said user interface. In yet another example, at 2466, the fractionalized electrode configuration may be stored in a storage device for future use.

Figure 25:
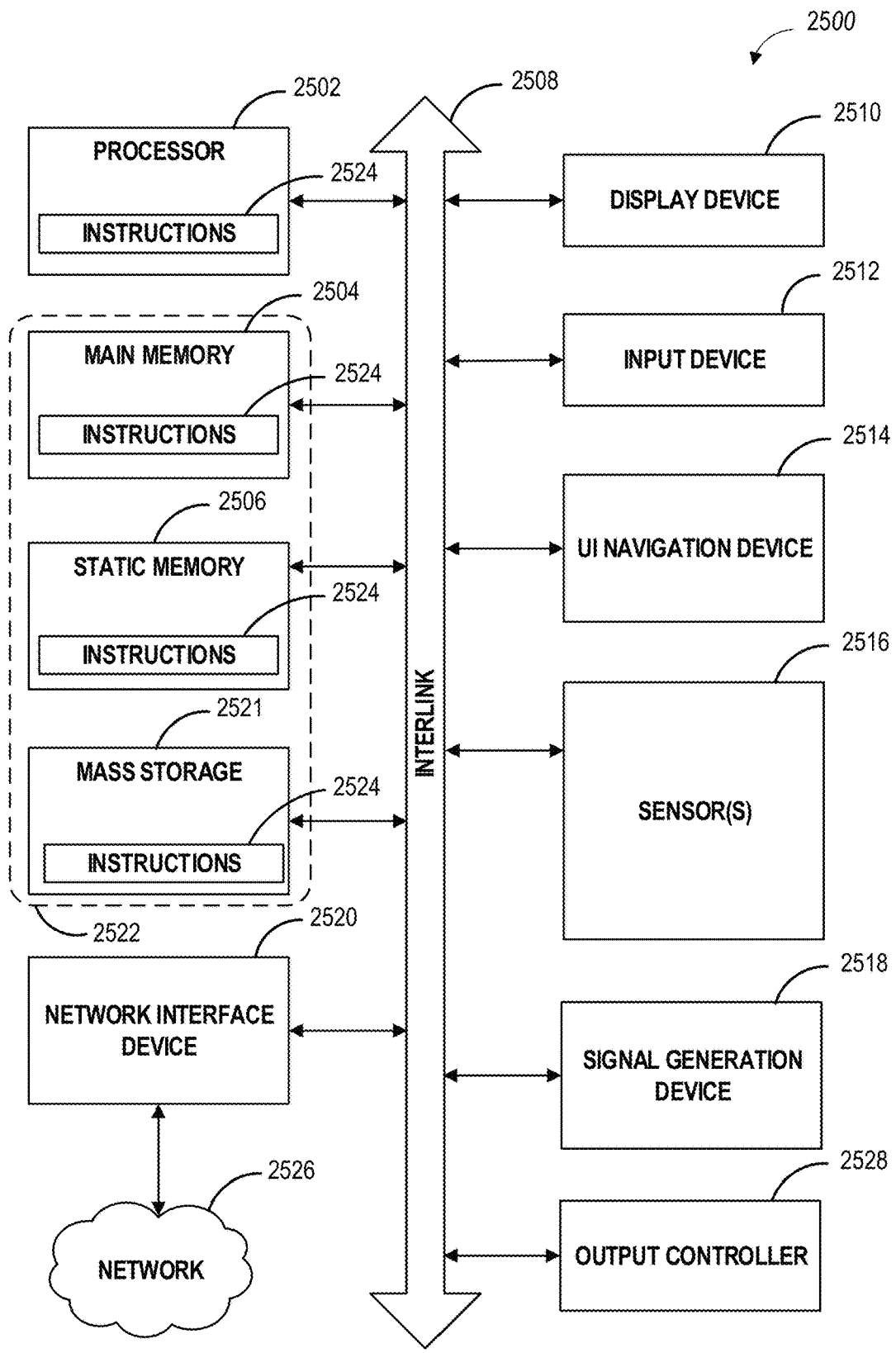
FIG. 25 illustrates generally a block diagram of an example machine 2500 upon which any one or more of the techniques (e.g., methodologies) discussed herein may perform.

FIG. 25 illustrates generally a block diagram of an example machine 2500 upon which any one or more of the techniques (e.g., methodologies) discussed herein may perform. Portions of this description may apply to the computing framework of various portions of the neuromodulation device or the external programming device.

In alternative embodiments, the machine 2500 may operate as a standalone device or may be connected (e.g., networked) to other machines. In a networked deployment, the machine 2500 may operate in the capacity of a server machine, a client machine, or both in server-client network environments. In an example, the machine 2500 may act as a peer machine in peer-to-peer (P2P) (or other distributed) network environment. The machine 2500 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 2500 may include a hardware processor 2502 (e.g., a central processing unit (CPU), a graphics processing unit (GPU), a hardware processor core, or any combination thereof), a main memory 2504 and a static memory 2506, some or all of which may communicate with each other via an interlink (e.g., bus) 2508. The machine 2500 may further include a display unit 2510 (e.g., a raster display, vector display, holographic display, etc.), an alphanumeric input device 2512 (e.g., a keyboard), and a user interface (UI) navigation device 2514 (e.g., a mouse). In an example, the display unit 2510, input device 2512 and UI navigation device 2514 may be a touch screen display. The machine 2500 may additionally include a storage device (e.g., drive unit) 2516, a signal generation device 2518 (e.g., a speaker), a network interface device 2520, and one or more sensors 2521, such as a global positioning system (GPS) sensor, compass, accelerometer, or other sensor. The machine 2500 may include an output controller 2528, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 2516 may include a machine readable medium 2522 on which is stored one or more sets of data structures or instructions 2524 (e.g., software) embodying or utilized by any one or more of the techniques or functions described herein. The instructions 2524 may also reside, completely or at least partially, within the main memory 2504, within static memory 2506, or within the hardware processor 2502 during execution thereof by the machine 2500. In an example, one or any combination of the hardware processor 2502, the main memory 2504, the static memory 2506, or the storage device 2516 may constitute machine readable media.

While the machine readable medium 2522 is illustrated as a single medium, the term "machine readable medium" may include a single medium or multiple media (e.g., a centralized or distributed database, and/or associated caches and servers) configured to store the one or more instructions 2524.

The term "machine readable medium" may include any medium that is capable of storing, encoding, or carrying instructions for execution by the machine 2500 and that cause the machine 2500 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 2524 may further be transmitted or received over a communications network 2526 using a transmission medium via the network interface device 2520 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 2520 may include one or more physical jacks (e.g., Ethernet, coaxial, or phone jacks) or one or more antennas to connect to the communications network 2526. In an example, the network interface device 2520 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 2500, and includes digital or analog communications signals or other intangible medium to facilitate communication of such software.

Various embodiments are illustrated in the figures above. One or more features from one or more of these embodiments may be combined to form other embodiments.

The method examples described herein may be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code may form portions of computer program products. Further, the code may be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A method for controlling neuromodulation therapy in a patient, the method comprising:
    receiving information of pain sites on a body surface of the patient;
    determining a dermatomal coverage of paresthesia over one or more dermatomes on the body surface in response to stimulation applied to a set of electrodes place on the patient at respective electrode locations;
    determining, via a controller circuit, an anodic weight and a cathodic weight for each of the electrode locations using (i) the received information of pain sites and (ii) the determined dermatomal coverage of paresthesia;
    determining or adjusting, via a controller circuit, a stimulation configuration based on the anodic and cathodic weights corresponding to one or more of the electrode locations; and
    delivering neuromodulation to the patient in accordance with the determined or adjusted stimulation configuration.

2. The method of claim 1, wherein determining the anodic weight and the cathodic weight is based on a spatial correspondence between the pain sites and the determined dermatomal coverage.

3. The method of claim 2, comprising:
    mapping the pain sites to one or more dermatomes; and
    determining the spatial correspondence by identifying one or more overlapping areas on the body surface between the mapped pain sites and paresthesia sites at the one or more dermatomes.

4. The method of claim 1, comprising receiving patient feedback on the paresthesia at one or more dermatomes in response to the stimulation applied to the set of electrodes,
    wherein determining the dermatomal coverage of paresthesia is based on the received patient feedback.

5. The method of claim 1, comprising sensing evoked response to the stimulation at the electrode locations via on or more sensing electrodes or sensors,
    wherein determining the dermatomal coverage of paresthesia is based on the sensed evoked response.

6. The method of claim 1, comprising receiving a patient comfort indicator indicating patient preference or side-effect in response to the stimulation applied to a set of electrodes,
    wherein determining the anodic weight and the cathodic weight further includes using the patient comfort indicator.

7. The method of claim 1, further comprising determining for each of the electrode locations a corresponding perception threshold of paresthesia,
    wherein determining the anodic weight or the cathodic weight further includes using the determined perception threshold.

8. The method of claim 1, wherein the neuromodulation delivered in accordance with the determined or adjusted stimulation configuration includes a paresthesia-free neuromodulation therapy.

9. A method for controlling neuromodulation therapy in a patient, the method comprising:
    receiving information of pain sites on a body surface of the patient;
    determining a dermatomal coverage of paresthesia over one or more dermatomes on the body surface in response to stimulation applied to a set of electrodes placed on the patient at respective electrode locations;
    determining or adjusting, via a controller circuit, a stimulation configuration based on a spatial correspondence between (i) the received information of pain sites and (ii) the determined dermatomal coverage of paresthesia; and
    delivering neuromodulation to the patient in accordance with the determined or adjusted stimulation configuration.

10. The method of claim 9, comprising:
    mapping the pain sites to one or more dermatomes; and
    determining the spatial correspondence by identifying one or more overlapping areas on the body surface between the mapped pain sites and paresthesia sites at the one or more dermatomes.

11. The method of claim 10, further comprising determining a cathodic weight and an anodic weight for each of the electrode locations,
    wherein determining or adjusting the stimulation configuration is based on the anodic and cathodic weights corresponding to one or more of the electrode locations.

12. The method of claim 9, further comprising receiving patient feedback on the paresthesia at one or more dermatomes in response to the stimulation applied to the set of electrodes,
    wherein determining the dermatomal coverage of paresthesia is based on the received patient feedback.

13. The method of claim 9, further comprising sensing evoked response to the stimulation at the electrode locations via on or more sensing electrodes or sensors,
    wherein determining the dermatomal coverage of paresthesia is based on the sensed evoked response.

14. The method of claim 9, further comprising receiving patient comfort indicator indicating patient preference or side-effect in response to the stimulation applied to a set of electrodes,
    wherein determining or adjusting the stimulation configuration further includes using the patient comfort indicator.

15. The method of claim 9, further comprising determining for each of the electrode locations a corresponding perception threshold of paresthesia, wherein determining or adjusting the stimulation configuration further includes using the determined perception threshold.

16. The method of claim 9, wherein the stimulation configuration includes one or more of a stimulation field parameter, a stimulation waveform pattern, or a current or energy fractionalization among the set of electrodes.

17. A system for controlling neuromodulation therapy in a patient, the system comprising:

an electrostimulator configured to stimulate target tissue of the patient via a set of electrodes at respective electrode locations according to a stimulation setting; and a controller circuit configured to:

receive information of pain sites on a body of the patient and a dermatomal coverage of paresthesia over one or more dermatomes on the patient body in response to the stimulation of the target tissue;

determine or adjust a stimulation configuration based on a spatial correspondence between the received information of pain sites and the dermatomal coverage of paresthesia; and generate a control signal to the electrostimulator to deliver a neuromodulation therapy in accordance with the determined or adjusted stimulation configuration.

18. The system of claim 17, wherein the neuromodulation therapy delivered in accordance with the determined or adjusted stimulation configuration includes a paresthesia-free neuromodulation therapy.

19. The system of claim 17, wherein the received dermatomal coverage includes one or more of patient feedback on the paresthesia at one or more dermatomes, or evoked sensed at the respective electrode locations, in responses to the stimulation.

20. The system of claim 17, wherein the stimulation configuration includes one or more of a stimulation field parameter, a stimulation waveform pattern, or a current or energy fractionalization among the set of electrodes.

* * * * *